United States Patent
Gill et al.

(10) Patent No.: US 7,505,813 B1
(45) Date of Patent: Mar. 17, 2009

(54) SYSTEM AND METHOD FOR DETERMINING PREFERRED ATRIOVENTRICULAR PACING DELAY VALUES BASED ON INTRACARDIAC ELECTROGRAM SIGNALS

(75) Inventors: Jong Gill, Valencia, CA (US);
Alexander Huemmer, Moehrendorf (DE); Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 570 days.

(21) Appl. No.: 11/199,619

(22) Filed: Aug. 8, 2005

(51) Int. Cl.
*A61N 1/00* (2006.01)

(52) U.S. Cl. .......................................................... 607/2

(58) Field of Classification Search ............... 607/18, 607/23, 25, 2
See application file for complete search history.

(56) References Cited

U.S. PATENT DOCUMENTS

| | | | |
|---|---|---|---|
| 4,108,148 A | 8/1978 | Cannon, III | |
| 5,179,949 A * | 1/1993 | Chirife | 607/9 |
| 5,330,511 A * | 7/1994 | Boute | 607/25 |
| 5,417,714 A * | 5/1995 | Levine et al. | 607/9 |
| 5,507,782 A | 4/1996 | Kieval et al. | |
| 5,814,077 A | 9/1998 | Sholder et al. | 607/9 |
| 5,873,895 A | 2/1999 | Sholder et al. | 607/9 |
| 6,122,546 A | 9/2000 | Sholder et al. | 607/9 |
| 6,351,673 B1 * | 2/2002 | Ding et al. | 607/24 |
| 6,650,931 B1 | 11/2003 | McClure et al. | |
| 6,882,882 B2 * | 4/2005 | Struble et al. | 607/9 |
| 6,937,902 B2 * | 8/2005 | Lidman et al. | 607/27 |
| 7,110,817 B2 * | 9/2006 | Yu et al. | 607/23 |
| 7,184,835 B2 * | 2/2007 | Kramer et al. | 607/9 |
| 2002/0151934 A1 | 10/2002 | Levine | 607/9 |
| 2002/0151935 A1 | 10/2002 | Levine | 607/9 |
| 2003/0014084 A1 | 1/2003 | VanHout | |
| 2003/0032991 A1 | 2/2003 | Poore | |
| 2003/0060850 A1 | 3/2003 | Zhu et al. | 607/9 |
| 2003/0083700 A1 | 5/2003 | Hill | |
| 2003/0144703 A1 * | 7/2003 | Yu et al. | 607/17 |
| 2005/0137630 A1 | 6/2005 | Ding et al. | |

FOREIGN PATENT DOCUMENTS

EP    0494487 B1    1/1996

OTHER PUBLICATIONS

Yu et al., "Optimization of AV Delay in DDD Mode of Cardiac Resynchronization Therapy for Heart Failure Patients," *EUROPACE Supplements*, vol. 4 (Dec. 2003), A30-6.

(Continued)

*Primary Examiner*—George Manuel

(57) ABSTRACT

Techniques are provided for use by an implantable medical device for determining optimal or preferred atrioventricular (AV) pacing delay values for use in pacing the heart. Briefly, the atria and ventricles are paced using an initial AV pacing delay set to a value less than an intrinsic AV conduction delay so that intrinsic ventricular depolarizations are avoided. An internal electrical cardiac signal is sensed and atrial evoked responses and subsequent ventricular evoked responses are identified therein. Time delays between the atrial and ventricular evoked responses are measured and then a preferred or optimal AV pacing delay value is determined based on: the initial AV pacing delay; the measured time delays between the atrial and ventricular evoked responses; and on a predetermined preferred time delay to be achieved between atrial and ventricular evoked responses. Similar procedures are employed in connection with atrial sensed events. A calibration procedure is also described.

17 Claims, 11 Drawing Sheets

OTHER PUBLICATIONS

Strohmer, Bernhard et al., "*Evaluation of Atrial Conduction Time at Various Sites of Right Atrial Pacing and Influence on Atrioventricular Delay Optimization by Surface Electrocardiography*," PACE, vol. 27 (Apr. 2004), pp. 468-474.

Strohmer B. et al., "AV-Delay Optimization Guided by Surface ECG: Impace on Stroke Volume in DDD Pacing," *EUROPACE* 2003.

Strohmer et al., "Validation of Total Atrial Conduction Time by Surface-ECG at Various Right Atrial Pacing Sites," *EUROPACE* 2003.

Koglek W. et al., "A Simple Method for AV-Delay Determination in Dual Chamber Pacemakers," *Herzschrittmachertherapie und Elektrophysiologie* (Herzschrittmacherther. Elecktrophysiol.)(Germany) 2000, 11/4 (244-253), (pp. 1-16 provided in English).

Levine, P., MD, FACC, "Programming the AV Delay; Supplement A" *Guidelines to the Routing Evaluation, Programming and Follow-Up of the Patient with an Implanted Dual-Chamber Rate Modulated Pacing System* 2003.

Chirife, Raul et al., "Automatic Beat-to-Beat Left Heart AV Normalization: Is It Possible?," PACE. 2003;26:2103-2110.

NonFinal Office Action, mailed Aug. 15, 2006: Related U.S. Appl. No. 10/928,586.

Notice of Allowance, mailed Mar. 23, 2007: Related U.S. Appl. No. 10/928,586.

* cited by examiner

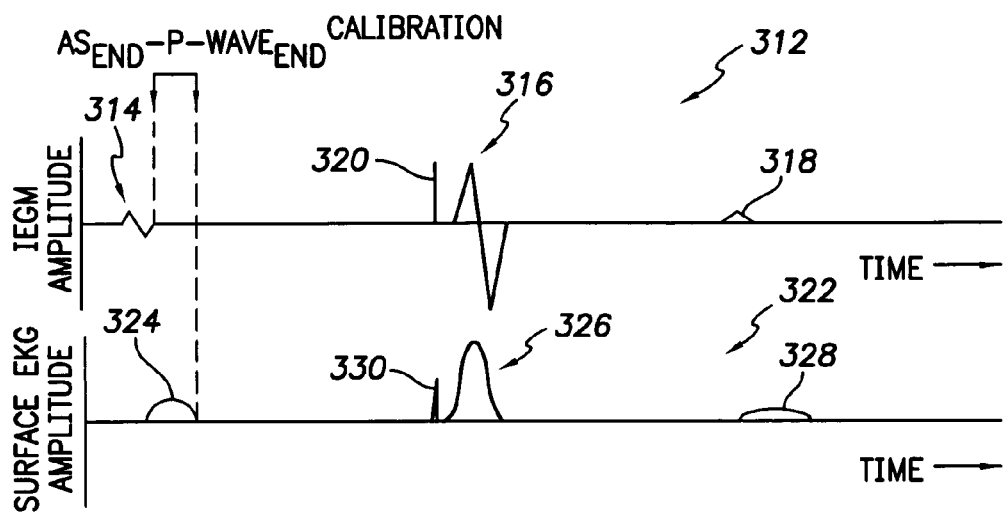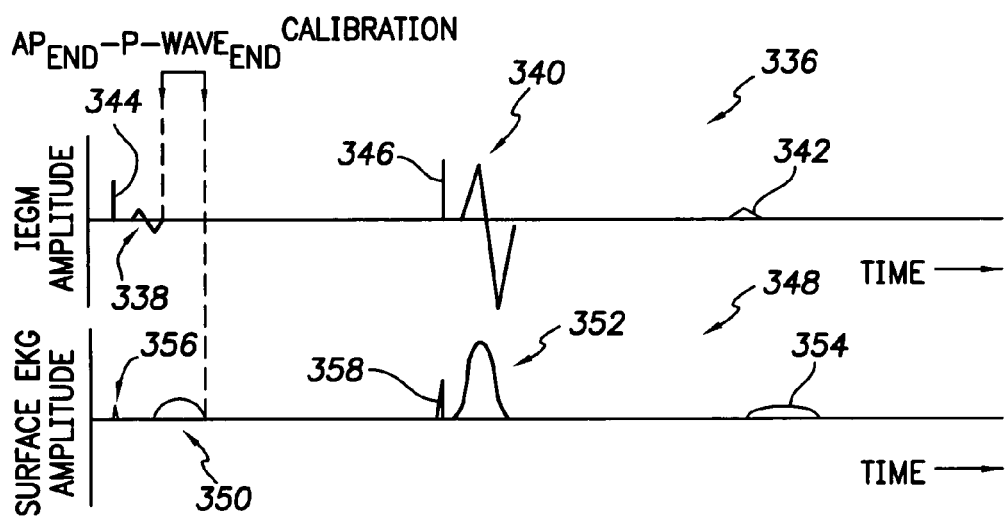
FIG. 7

US 7,505,813 B1

SYSTEM AND METHOD FOR DETERMINING PREFERRED ATRIOVENTRICULAR PACING DELAY VALUES BASED ON INTRACARDIAC ELECTROGRAM SIGNALS

CROSS REFERENCE TO RELATED APPLICATIONS

This application is related to U.S. Pat. No. 7,248,925 filed Aug. 27, 2004, titled "System and Method for Determining Optimal Atrioventricular Delay Based on Intrinsic Conduction Delays."

FIELD OF THE INVENTION

The invention generally relates to implantable medical devices for use in pacing the heart of a patient and in particular to techniques for determining preferred or optimal atrioventricular (AV) pacing delay times for individual patients based on intracardiac electrogram (IEGM) signals.

BACKGROUND OF THE INVENTION

Implantable medical devices, particularly pacemakers and implantable cardioverter defibrillators (ICDs), are typically configured to be used in conjunction with an external programmer that enables a physician to program the operation of an implanted device to, for example, control the specific parameters by which the pacemaker detects arrhythmia conditions and responds thereto. For instance, the physician may specify the sensitivity with which the pacemaker or ICD senses electrical signals within the heart and also specify the amount of electrical energy to be employed in pacing pulses or defibrillation shocks. Other common control parameters include AV pacing delay values, which for dual chamber devices specify time delays between events sensed in the atria and pacing pulses to be delivered to the ventricles and/or time delays between atrial pacing pulses and ventricular pacing pulses. Additionally, the external programmer may be configured to receive and display a wide variety of diagnostic information detected by the implantable device, such as IEGM signals sensed by the device, as well as diagnostic data from other sources, such as surface electrocardiogram (EKG) systems.

For many patients, particularly those with congestive heart failure (CHF), it is desirable to identify a set of control parameters that will yield optimal cardiac performance (also referred to as hemodynamic performance). Cardiac performance is a measure of the overall effectiveness of the cardiac system of a patient and is typically represented in terms of stroke volume or cardiac output. Stroke volume is the amount of blood ejected from the left ventricle during systole in a forward direction. Cardiac output is the volume of blood pumped by the left ventricle per minute (or stroke volume times the heart rate). In view of the importance of maintaining optimal cardiac performance, especially for patients with compromised cardiac function, it would be desirable to provide improved techniques for use with pacemakers or ICDs for identifying pacing control parameters that optimize cardiac performance, particularly to reduce the degree of heart failure and valvular regurgitation. It is to this end that aspects of the invention are generally directed.

It is particularly desirable to identify AV pacing delay values that provide the best cardiac performance for a particular patient. In normal patients, the electrical conduction through the AV node is intact, and the body automatically adjusts the delay via the circulating hormones and the autonomic nervous system according to its physiologic state. It is well known, for example, that in normal patients, the intrinsic AV delay shortens with increasing heart rate associated with a physiologic stress such as exercise. For patients with abnormal AV node conduction or complete heart block, a pacemaker can control the AV pacing delay by delivering a ventricular pacing pulse at a software-controlled delay after an atrial pulse or intrinsic atrial depolarization. Since the optimum AV delay values vary from person to person, these parameters should be optimized on an individual basis.

Conventionally, the physician attempts to program the AV pacing delay for a given patient by using an external programmer to control the device implanted within the patient to cycle through a set of different AV pacing delay values. For each value, the implanted device paces the heart of the patient for at least a few minutes to permit hemodynamic equilibration, then the physician records a measure of the resulting cardiac performance obtained, for example, using Doppler echocardiography. The AV pacing delay that yields the best cardiac performance is then selected and programmed into the device. However, this is a time consuming and potentially expensive procedure. As a result, some physicians do not bother to optimize the AV pacing delay in many of their patients. Rather, the AV pacing delay is merely set to a default value and is adjusted only if the patient does not respond well to pacing therapy. Hence, many patients are not paced at their particular optimal AV pacing delay value and thus do not obtain the maximal potential benefit from the improved cardiac performance that could otherwise be gained. Moreover, even in circumstances wherein AV pacing delay is optimized by the physician using, for example, Doppler echocardiography, the time and associated costs are significant. In addition, the optimal AV pacing delay for a particular patient may change with time due to, for example, progression or regression in CHF, changes in medications, and/or changes in overall fitness. However, with conventional optimization techniques, the AV pacing delay is re-optimized, if at all, only during specially scheduled follow-up sessions with the physician to allow access to the noninvasive testing equipment such as Doppler-echocardiography, which may be months or perhaps years apart. In addition, separate AV pacing delay values are typically not obtained for use with paced or sensed atrial events. Usually, PV delay is set to be shorter than AV delay when programming either PV or AV delay.

Recently, optimization techniques have been proposed that do not require Doppler-echocardiography but instead use only the surface EKG. See, Strohmer et al., "Evaluation of Atrial Conduction Time at Various Sites of Right Atrial Pacing and Influence on Atrioventricular Delay Optimization by Surface Electrocardiography," PACE, Vol. 27, April 2004, pp 468-474. Strohmer et al. propose that the AV pacing delay be set based on a surface EKG so as to achieve a 100 millisecond (ms) delay between the end of the P-wave and the peak of the R-wave of the surface EKG. Although an EKG-based technique, such as that of Strohmer et al. eliminates the need to employ Doppler-echocardiography it would instead be desirable to provide techniques that can be performed using IEGM data so that the optimization may be performed by the device itself allowing the AV pacing delay to be automatically and frequently updated in response to change within the patient.

One technique that utilizes IEGM data is set forth in U.S. patent application Ser. No. 10/928,586 of Bruhns et al. filed Aug. 27, 2004, entitled "System and Method for Determining Optimal Atrioventricular Delay Based on Intrinsic Conduction Delays." Briefly, with the technique of Bruhns et al. intrinsic inter-atrial conduction delays and intrinsic AV conduction delays are determined for the patient and then optimal AV pacing delays are derived therefrom. In one example, the technique uses only IEGM signals and hence can be performed by the device itself without the use of a surface EKG. This permits optimal AV pacing delays to be frequently and automatically updated so as to respond to changes within the patient. In another example, a surface EKG is used to aid in the determination of the inter-atrial conduction delay. In either case, Doppler-echocardiography is not required. The patent application of Bruhns et al. is assigned to the assignee of the present invention and is fully incorporated by reference herein.

Another technique that utilizes IEGM data is set forth in Yu et al., Europace Supplements, Vol. 4, December 2003: A30-6: "Optimization of AV Delay in DDD Mode of Cardiac Resynchronization Therapy for Heart Failure Patients." With the technique of Yu et al., the AV pacing delay be set to equal to 0.7 (AS–VS)–55 milliseconds (ms), where AS–VS represents the intrinsic AV delay, i.e. the delay between an intrinsic atrial depolarization and an intrinsic ventricular depolarization. Although this allows the AV pacing delay to be set automatically by the implanted device, it is not believed that the formula reliably provides the optimal delay value for many patients. In particular, it does not necessarily achieve a 100 ms delay between the end of the P-wave and the peak of the R-wave, which appears to be optimal. In addition, it does not provide for separate determination of optimal delay values for paced and sensed events.

Accordingly, it would be highly desirable to provide IEGM-based AV pacing delay optimization techniques, which substantially achieve the aforementioned 100 ms delay between the end of a P-wave and the peak of the R-wave for use with either paced or sensed atrial events, but which do not require the use of a surface EKG or require one only during an initial calibration step. It is to this end that the invention is directed.

In terms of nomenclature and abbreviations used herein, "A" is generally used to refer to atrial events, whether paced or sensed, occurring within internal electrical cardiac signals such as an IEGM. "V" is used to generally refer to ventricular events, whether paced or sensed, occurring within the internal electrical cardiac signal. In circumstances where it is necessary to distinguish between paced and sensed events, an "S" or "P" is appended. Hence, AS refers to a sensed atrial event, whereas AP refers to paced atrial event. VS refers to a sensed ventricular event, whereas VP refers to a paced ventricular event. A–V represents the delay between either a paced or sensed atrial event and a paced ventricular event. As already noted, "AV" is simply an abbreviation for "atrioventricular" and should not be confused with A–V, which represents a time delay value.

In circumstances where it is necessary to identify a specific point within an event, such as its beginning, peak or end, an appropriate subscript is also added. As examples, $AS_{END}$ represents the end of a sensed atrial event and $VP_{PEAK}$ represents the peak of a paced ventricular event. Herein, "peak" refers to the peak of the absolute value of a signal. Depending upon signal polarity, the peak may be positive or negative (i.e. a nadir.) Sensed events are also referred to herein as depolarizations as they are representative of electrical depolarization of myocardial tissue. Paced events are also referred to herein as evoked responses. Paced events in the atria are triggered by $A_{PULSES}$, which are electrical pacing pulses delivered by the implanted device to the atria. Paced events in the ventricles are triggered by $V_{PULSES}$, which are electrical pacing pulses delivered by the implanted device to the ventricles. The delay between an $A_{PULSE}$ and a $V_{PULSE}$ is referred to herein as $A_{PULSE}-V_{PULSE}$ and should not be confused with AP–VP, which instead represents the delay between an atrial evoked response triggered by an $A_{PULSE}$ and a ventricular evoked response triggered by a $V_{PULSE}$. Similarly, AS–$V_{PULSE}$ represents the time delay between an intrinsic atrial depolarization and a $V_{PULSE}$ and should not be confused with AS–VP, which instead represents the delay between the atrial depolarization and the ventricular evoked response. $A_{PULSE}-V_{PULSE}$ and AS–$V_{PULSE}$ correspond to the aforementioned AV pacing delay values for paced and sensed atrial events. In circumstances where it is desirable to identify an "initial" delay value or a "preferred" delay value, appropriate superscripts are employed, such as AS–$V_{PULSE}^{INITIAL}$ or $A_{PULSE}-V_{PULSE}^{PREFERRED}$, where AS–$V_{PULSE}^{PREFERRED}$ specifies an initial value of the AS–$V_{PULSE}$ delay and $A_{PULSE}-V_{PULSE}^{PREFERRED}$ specifies a preferred value for the $A_{PULSE}-V_{PULSE}$ delay. Where appropriate, an "L" or "R" subscript may be employed to distinguish between the left and right chambers of the heart. For example, $AP_R$ refers to a paced event in the right atrium. $VS_R$ refers to a sensed event in the right ventricle.

The term "intrinsic delay," as used herein, refers to the delay between a paced or sensed event in one chamber and a subsequent depolarization in another chamber. For example, an "intrinsic AV delay" refers to the delay between a paced or sensed atrial event and a subsequent sensed ventricular event, e.g. an AS–VS or AP–VS delay. Note also that electrical events detected within an internally sensed electrical cardiac signal typically correspond to events detectable within a surface EKG. In this regard, the P-wave of the surface EKG generally corresponds to either an atrial sensed event (AS) or an atrial paced event (AP) with the IEGM; the R-wave of the surface EKG generally corresponds to either a ventricular sensed event (VS) or a ventricular paced event (VP) with the IEGM. The T-wave of the surface EKG generally corresponds to a ventricular repolarization event of the IEGM. The events within the surface EKG, however, may differ from the corresponding events within the IEGM as to both timing and shape.

SUMMARY OF THE INVENTION

In accordance with the invention, techniques are provided for determining preferred or optimal AV pacing delay values for use in delivering cardiac pacing therapy to the heart of a patient in which an implantable medical device is implanted. Briefly, the heart is paced using an initial AV pacing delay set to a value less than an intrinsic AV conduction delay so that intrinsic ventricular depolarizations are avoided. An internal electrical cardiac signal is sensed and at least one atrial event and subsequent paced ventricular event are identified therein. The time delay between the atrial event and the paced ventricular event is measured and then a preferred or optimal AV pacing delay value is determined based on: the initial AV pacing delay; the measured time delay between the atrial event and the paced ventricular event; and on a predetermined preferred time delay to be achieved between atrial events and subsequent paced ventricular events.

In one example, the technique is performed to determine the AV pacing delay that will yield a preferred time delay between sensed atrial events and subsequent paced ventricular events. In other words, the technique operates to determine the particular pacing time delay value needed between an intrinsic atrial depolarization (AS) and the subsequent VPULSE so as to achieve a specified preferred time delay between the atrial depolarization and the ventricular evoked response (VP) that is triggered by the subsequent $V_{PULSE}$. In the example, the heart is first paced subject to the initial AV pacing delay value, i.e. intrinsic atrial depolarizations are detected and then $V_{PULSES}$ are delivered to the ventricles at a later time as specified by the initial AV pacing delay value. The resulting ventricular evoked responses are detected and the average time delay from atrial depolarization to ventricular evoked response is measured. The implanted device then determines the AV pacing delay value needed to achieve the specified time delay between atrial depolarization and the ventricular evoked response using:

$$AS\text{-}V_{PULSE}^{PREFERRED} = AS\text{-}V_{PULSE}^{INITIAL} + AS\text{-}VP^{PREFERRED} - AS\text{-}VP^{OBSERVED}$$

where $AS\text{-}V_{PULSE}^{INITIAL}$ is the initial AV pacing delay that is typically programmable in current devices, $AS\text{-}VP^{PREFERRED}$ is the delay value to be achieved between an atrial depolarization and the ventricular evoked response triggered by the subsequent $V_{PULSE}$, $AS\text{-}VP^{OBSERVED}$ is the measured delay value, and $AS\text{-}V_{PULSE}^{PREFERRED}$ is the resulting preferred or optimal AV pacing delay value for use with sensed atrial events.

In a specific example, the desirable $AS\text{-}V_{PULSE}$ delay value is achieved based on the end of the atrial depolarization and the peak of the ventricular evoked response. Accordingly, the device detects the ends of atrial depolarizations and the peaks of ventricular evoked responses and measures the average time delay therebetween. The implanted device then determines the AV pacing delay value needed to achieve the specified time delay using:

$$AS\text{-}V_{PULSE}^{PREFERRED} = AS\text{-}V_{PULSE}^{INITIAL} + AS_{END}\text{-}VP_{PEAK}^{PREFERRED} - AS_{END}\text{-}VP_{PEAK}^{OBSERVED}$$

where $AS\text{-}V_{PULSE}^{INITIAL}$ is the initial AV pacing delay, $AS_{END}\text{-}VP_{PEAK}^{PREFERRED}$ is the delay value to be achieved between the end of the atrial depolarization and the peak of the ventricular evoked response, and $AS_{END}\text{-}VP_{PEAK}^{OBSERVED}$ is the measured delay value between the end of the atrial depolarization and the peak of the ventricular evoked response. The initial AV pacing delay, $AS\text{-}V_{PULSE}^{INITIAL}$ may be set, for example, to 200 ms. An exemplary value for $AS_{END}\text{-}VP_{PEAK}^{PREFERRED}$ is 100 ms. If the measured $AS_{END}\text{-}VP_{PEAK}^{OBSERVED}$ turns out to be 170 msec, then the optimal AV pacing delay, $AS\text{-}V_{PULSE}^{PREFERRED}$ is 200 ms+100 ms−170 ms=130 ms. If desired, the time delay to be achieved may be specified based on the delay between the end of a P-wave and the peak of an R-wave within a surface EKG, rather than based on time delays between events within the IEGM. If so, then the value of $AS_{END}\text{-}VP_{PEAK}^{OBSERVED}$ is preferably adjusted using a calibration offset value input to the device that is representative of an average time delay between the ends of atrial depolarizations observed within the IEGM and the ends of corresponding P-waves within the surface EKG as measured during an initial calibration procedure following device implant.

Similar steps are performed to determine the AV pacing delay that will yield a preferred time delay between paced atrial events and subsequent paced ventricular events. In other words, a technique is provided that operates to determine the $A_{PULSE}\text{-}V_{PULSE}$ delay needed to achieve a specified preferred time delay between an atrial evoked response (AP) triggered by a $A_{PULSE}$ and the ventricular evoked response (VP) triggered by a $V_{PULSE}$. In a specific example, the delay value to be achieved is specified based on the end of the atrial evoked response ($AP_{END}$) and the peak of the ventricular evoked response ($VP_{PEAK}$). Accordingly, the device measures the average observed value of the $AP_{END}\text{-}VP_{PEAK}$ time delay value for use in determining $A_{PULSE}\text{-}V_{PULSE}$ delay.

It is believed that the preferred AV pacing delay values calculated in this manner represent optimal delay values in that the values tend to maximize ventricular filling so as to maximize cardiac performance. However, even if the delay values differ from true optimal values, they nevertheless represent preferred delay values likely to improve ventricular filling. Preferably, separate pacing delay values for use with paced and sensed atrial events (i.e. separate $AS\text{-}V_{PULSE}$ and $A_{PULSE}\text{-}V_{PULSE}$ values) are calculated and used. Alternatively, a preferred $AS\text{-}V_{PULSE}$ value can be calculated using the techniques of the invention for use in conjunction with an $A_{PULSE}\text{-}V_{PULSE}$ value selected using otherwise conventional techniques, or vice versa.

Thus, improved techniques are provided for more easily and reliably determining preferred or optimal AV pacing delay values for a particular patient. The techniques may be performed by an implanted medical device based on internal cardiac signals thus permitting the preferred AV pacing delay values to be frequently and automatically updated to respond to any changes within the patient. Moreover, as noted, separate pacing delay values are determined for use with paced or sensed atrial events to provide for further optimization. In one example, an initial calibration step is performed using a surface EKG following device implant so as to obtain offset values for use in adjusting certain measured delay values. Otherwise, the use of a surface EKG is not required. System and method implementations are set forth.

BRIEF DESCRIPTION OF THE DRAWINGS

The above and further features, advantages and benefits of the invention will be apparent upon consideration of the present description taken in conjunction with the accompanying drawings, in which:

FIG. 7 provides a set of graphs illustrating calibration offset values obtained from a surface EKG for use with the technique of FIG. 6;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Figure 1:
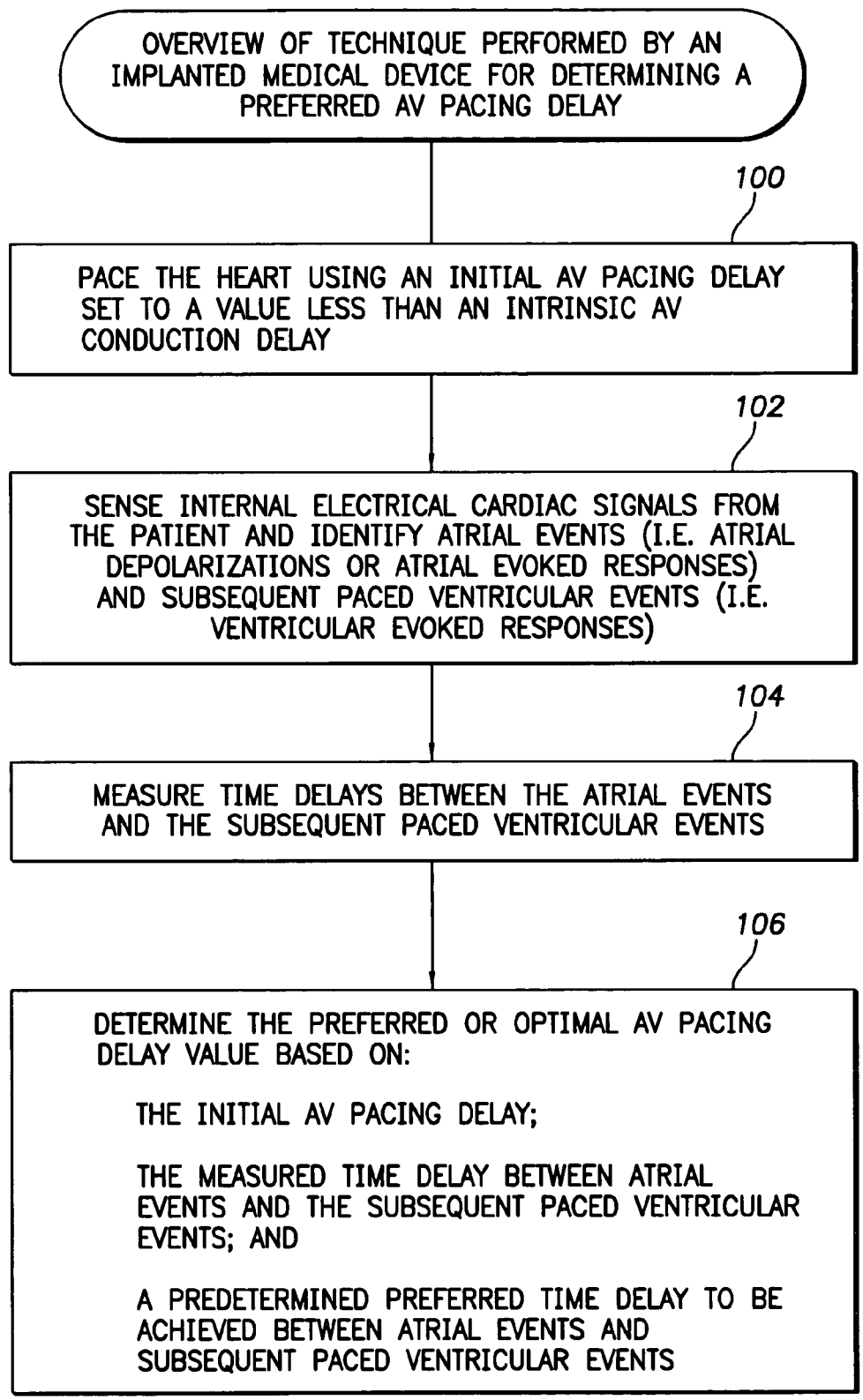
FIG. 1 is a flow chart providing an overview of techniques performed by an implantable medical device in accordance with the invention for determining preferred or optimal AV pacing delay values.

Briefly, an overview of the AV pacing delay optimization techniques of invention will first be provided with reference to FIG. 1. Then, exemplary techniques requiring no initial calibration will be described with reference to FIGS. 2-5. Next, exemplary techniques that employ an initial calibration step performed by an external programmer using a surface EKG will be described with reference to FIGS. 6-8. Finally, details of an exemplary implantable medical device and an exemplary external programmer will be provided with reference to FIGS. 9-11.

Overview of Technique for Determining Preferred AV Pacing Delay Values

Briefly, the technique operates to determine a preferred AV pacing delay (i.e. the time delay between atrial pulses and the subsequent ventricular pulses or the time delay between intrinsic atrial depolarizations and subsequent ventricular pulses) by specifying the preferred or optimal time delay to be achieved between paced or sensed atrial events and subsequent ventricular evoked responses. The technique then determines the AV pacing delay needed to achieve that specified time delay, which is referred to herein as the preferred AV pacing delay. Thereafter, when the heart is paced using the preferred AV pacing delay, the actual delay occurring between paced or sensed atrial events and subsequent ventricular evoked responses will then be substantially equal to the preferred time delay originally specified. Separate preferred AV pacing time delays may be determined for use with paced and sensed atrial events. In one specific implementation, described below, the preferred time delay to be achieved is specified between the ends of atrial events and the peaks of subsequent ventricular evoked responses. FIG. 1, however, provides an overview that does not distinguish between paced or sensed events and which does not specify the particular locations within the various events for timing the delays (i.e. beginning, peak or end).

At step 100, the heart of the patient is paced using an implantable medical device such as a pacemaker or ICD in accordance with otherwise conventional AV pacing techniques wherein the device detects intrinsic atrial depolarizations indicative of an atrial contraction using electrodes implanted in the atria and then delivers ventricular pacing pulses using electrodes implanted within the ventricles to cause the ventricles to contract. The ventricular pacing pulse is delivered prior to a next expected ventricular depolarization so as to allow the time delay between atrial and ventricular contractions to be controlled by the device. If no intrinsic atrial depolarization is detected within an expected time frame (indicating that the atria failed to properly contract in response to a native electrical signal generated by the sinus node of the heart), the device delivers an atrial pulse to cause the atria to contract, then delivers a ventricular pulse to cause ventricles to contract. As already explained, the time delay between the intrinsic atrial depolarization or atrial pacing pulse and the subsequent ventricular pacing pulse is the AV pacing delay, which the invention seeks to optimize.

The AV pacing delay used at step 100 is set to a value less than a predetermined intrinsic AV conduction delay of the patient. The intrinsic AV conduction delay specifies the time delay of electrical signals from the atria to the ventricles via normal conduction channels. In case of a completely pacemaker or ICD dependent patient in whom the AV node is ablated, the intrinsic AV conduction does not exist so that the ventricle will have to be paced 100% based on the programmed AV pacing delay. By setting the AV pacing delay to value less than the intrinsic conduction delay, it can be substantially assured that the ventricles will not spontaneously depolarize prior to delivery of the ventricular pulse. Accordingly, the intrinsic AV conduction delay is preferably determined by the device prior to performing the optimization steps of FIG. 1. This may be done in accordance with otherwise conventional techniques. In one example, the implanted device allows the ventricles to beat naturally (i.e. without ventricular pacing pulses) and monitors time delays between paced or sensed atrial events and intrinsic ventricular depolarizations. The average time delay represents the intrinsic AV conduction delay. In any case, the initial AV pacing delay is then set less than the intrinsic conduction delay. In this manner, the intrinsic conduction delay specifies a maximum value for the initial AV conduction delay. A minimum value is preferably set as well so that the ventricles will not be paced too promptly following an atrial contraction, which might impair the hemodynamics of the heart. In one example, the minimum value for the AV pacing delay is 50 ms. The maximum value is 250 ms. Note that the initial AV pacing delay used at step 100 may be arbitrarily set anywhere within that range. Indeed, it is one of the advantages of the invention that the initial AV pacing delay need not be set to any specific initial value. Rather, it is sufficient to set the initial AV pacing delay value to any arbitrary value with the range of acceptable values and the techniques and invention will nevertheless determine the preferred AV pacing delay using that initial delay.

At step 102, the implanted device senses internal electrical cardiac signals (such as IEGM signals) from the patient and identifies atrial events and subsequent paced ventricular events, i.e. the device identifies an intrinsic atrial depolarizations, atrial evoked responses, and ventricular evoked responses. At step 104, the device measures time delays between the atrial events and the subsequent paced ventricular events. Then, at step 106, the device determines a preferred or optimal AV pacing delay value based on: the initial AV pacing delay, which had been arbitrarily selected; the measured time delay between atrial events and subsequent paced ventricular events; and the predetermined preferred time delay to be achieved between atrial events and subsequent paced ventricular events. As already explained, the preferred AV pacing delay value is the time delay value needed to time delivery of ventricular pulses so as to achieve the specified time delay between paced and sensed atrial events (not the atrial pulses themselves) and subsequent paced ventricular events (not the ventricular pulses themselves.) Techniques for calculating the preferred AV pacing delay that will achieve the specified time delay are described in detail below with reference to FIGS. 3 and 6. The specified time delay to be achieved is preferably programmed into the implanted device using an external device programmer following initial device implant so as to permit the physician to review the specified value and to adjust it, if desired. In one specific example discussed below, the preferred time delay is specified between the end of an atrial event and the peak of the ventricular evoked response and is programmed to 100 ms.

Using these techniques, preferred AV pacing delay values can be reliably determined without requiring complicated conventional optimization techniques such as the use of Doppler echocardiography and the like. Moreover, the preferred pacing delay values can be determined by the implantable device itself and recalculated as often as needed, based upon newly sensed IEGM signals, to update the values in response to changing conditions in the patient. Hence, the patient benefits from improved cardiac performance.

Figure 2:
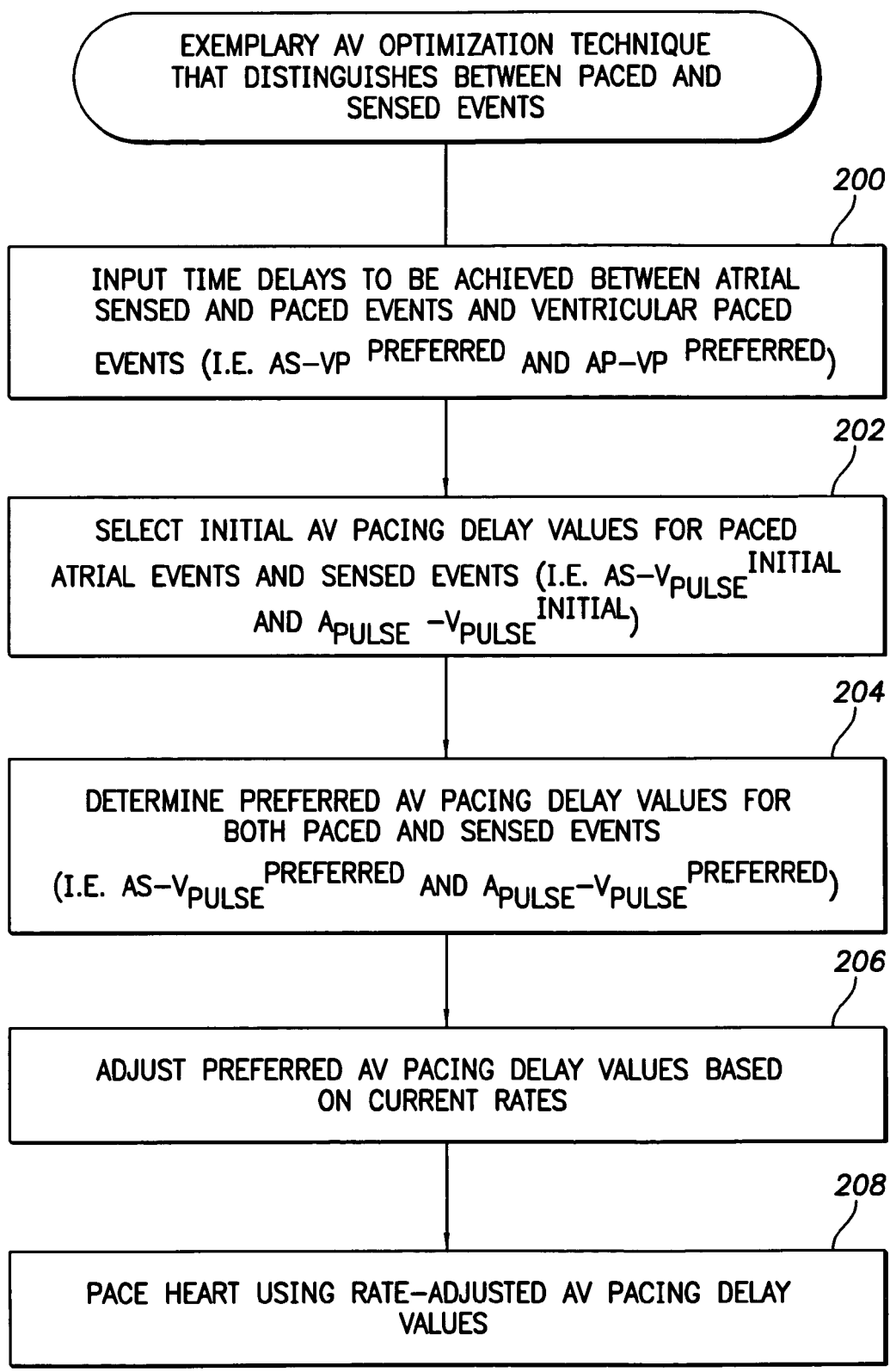
FIG. 2 is a flow chart illustrating an exemplary technique for determining preferred AV pacing delay values for paced and sensed events, in accordance with the general techniques of FIG. 1, and for adjusting the preferred delay values based on rate.

Exemplary Optimization Technique for Separately Determining AV Pacing Delay Values for Both Paced and Sensed Events Turning now to FIGS. 2-8, various exemplary techniques will be described for separately determining preferred AV pacing delay values for paced and sensed events and for adjusting the preferred pacing delay values based upon current heart rate or pacing rate. Referring first to FIG. 2, beginning at step 200, an optimization system within the implanted device inputs from memory a pair of preferred time delay values to be achieved—one for use with sensed atrial events, the other for paced atrial events. In other words, a preferred time delay for use with sensed atrial events (i.e. AS–$VP^{PREFERRED}$) is input, which specifies the preferred or optimal time delay to be achieved between an intrinsic atrial depolarization (AS) and a subsequent ventricular evoked response (VP) triggered by a ventricular pulse ($V_{PULSE}$). A separate preferred time delay for use with paced atrial events (i.e. AP–$VP^{PREFERRED}$) is input, which specifies the preferred or optimal time delay to be achieved between an atrial evoked response (AP) and a subsequent ventricular evoked response (VP). The specific values originally programmed into memory will depend upon the precise features of the various events used to measure the time delays, i.e. the beginning, the peak or the end. In an example described with reference to FIGS. 3 and 4, the time delays are specified between the ends of the atrial events and the peaks of the ventricular events. Other choices, however, may be made. The AS–$VP^{PREFERRED}$ and AP–$VP^{PREFERRED}$ values can be varied with rate.

At step 202, the optimization system selects a pair of initial AV pacing delay values—one for use with sensed atrial events and one for paced atrial events. That is, an initial pacing delay for use with atrial sensed events (i.e. AS–$V_{PULSE}^{INITIAL}$) is chosen and a separate initial pacing delayed for use with atrial paced events (i.e. $A_{PULSE}$–$V_{PULSE}^{INITIAL}$) is also chosen. As already noted, the initial values may be arbitrarily selected from within a range of acceptable pacing delay values. More specifically, AS–$V_{PULSE}^{INITIAL}$ is selected from within a range from AS–$V_{PULSE}^{MIN}$ to AS–$V_{PULSE}^{MAX}$. $A_{PULSE}$–$V_{PULSE}^{INITIAL}$ is selected from within a range from $A_{PULSE}$–$V_{PULSE}^{MIN}$ to $A_{PULSE}$–$V_{PULSE}^{MAX}$. The minimum values represent the shortest delay values that may be safely used for the patient without significant reduction in cardiac function. The maximum values represent the longest delay values that may be used for the patient without significant risk of an intrinsic ventricular depolarization (VS) occurring before the $V_{PULSE}$ is delivered. These values may be determined in advance in accordance with otherwise conventional techniques and programmed into the implanted device or may be periodically determined by the device by itself. Insofar as AS–$V_{PULSE}^{INITIAL}$ delay is concerned, the specific range of acceptable values may depend upon the particular feature of the atrial sensed event used to time subsequent delivery of the $V_{PULSE}$, i.e. the beginning, peak or end. $A_{PULSES}$ and $V_{PULSES}$ are usually very narrow voltage spikes and hence there is typically no need to distinguish between their beginnings, peaks or ends. However, within any pacing devices that might instead provide a broad pulse rather than a narrow spike, the various time delays referred to herein may be specified with respect to the beginnings, peaks or ends of those broad pulses.

At step 204, the optimization system of the implanted device then determines the preferred AV pacing delay values for paced and sensed events (i.e. AS–$V_{PULSE}^{PREFERRED}$ and $A_{PULSE}$–$V_{PULSE}^{PREFERRED}$) using the techniques generally explained above with respect to FIG. 1. As already mentioned, it is believed that the preferred AV pacing delay values calculated in this manner represent optimal delay values in that the values tend to maximize ventricular filling so as to maximize cardiac performance. However, even if the delay values differ from true optimal values, they nevertheless represent preferred delay values likely to improve ventricular filling. Exemplary techniques for use at step 204 are described below in greater detail with reference to FIGS. 3 and 6.

At step 206, the optimization system then automatically adjusts the preferred AV pacing delay values based upon current heart rate or base pacing rate. That is, the preferred AV pacing delay value for use with sensed atrial events is adjusted based on the current intrinsic heart rate of the patient, i.e. the current average time delay between atrial sensed events (AS–AS) The preferred AV pacing delay for use with paced atrial events is adjusted based on the current pacing rate used by the device, i.e. the current average time delay between atrial pulses ($A_{PULSE}$–$A_{–PULSE}$.) Exemplary techniques for adjusting the AV pacing delay values are described below with reference to FIG. 5. Finally, a step 208, pacing components of the implanted device pace the heart using the rate-adjusted AV pacing delay values determined by the optimization system. In this manner, the heart of the patient is paced using preferred or optimal AV pacing delay values, adjusted as needed based on the current intrinsic rate or pacing rate of the patient, so as to improve or optimize overall cardiac function. Preferably, steps 200-204 are repeated frequently to periodically update the AV pacing values so as to automatically compensate for any changes in the patient, such as changes that may be due to newly prescribed medications or to the onset or progression of heart failure. In one example, the optimization procedure is performed once per hour.

Exemplary Optimization Technique Based on Ends of Atrial Events and Peaks of Ventricular Events Turning now to FIGS. 3 and 4, a specific example for determining preferred AV pacing delays for use with step 204 of FIG. 2 will be described, wherein time delay values are measured between the ends of atrial events ($AS_{END}$ and $AP_{END}$) and the peaks of the ventricular evoked responses ($VP_{END}$). As such, the preferred delays to be achieved for sensed and paced atrial events (input at step 200 of FIG. 2) are specified as $AS_{END}$-$VP_{PEAK}^{PREFERRED}$ and $AP_{END}$-$VP_{PEAK}^{PREFERRED}$, respectively. In an exemplary implementation, wherein the IEGM signals processed by the optimization system are sensed between a right atrial tip (RAT) electrode and the device case, these preferred values are both set to 100 ms. In other cases, the values may differ from one another. The initial AV pacing delays for use with sensed and paced atrial events (selected at step 202 of FIG. 2) are specified as $AS$-$VP_{PULSE}^{INITIAL}$ and $A_{PULSE}$-$VP_{PULSE}^{INITIAL}$, respectively. As already noted, the initial AV pacing delay values may be arbitrarily selected from within a range of acceptable AV delay values. In one example, these values are both set to 200 ms. In other cases, the values may differ from one another. Steps performed based on atrial sensed events are shown on the left-hand side of FIG. 3. Steps performed based on paced atrial events are shown on the right-hand side of FIG. 2.

Referring first to the processing of sensed atrial events, at step 210, the implantable device detects intrinsic atrial depolarizations (AS) and identifies the ends thereof ($AS_{END}$). Techniques for conveniently identifying the ends of electrical events within IEGM signals (including depolarization events and evoked responses) are set forth in the above-referenced patent application to Bruhns et al. At step 212, the implantable device delivers $V_{PULSES}$ to the ventricles of patient at times specified by $AS$-$VP_{PULSE}^{INITIAL}$ (Note that the initial AV delay, i.e. $AS$-$VP_{PULSE}^{INITIAL}$, is not designated herein as with respect to the AS peak or end, since the device does not typically, specifically identify $AS_{PEAK}$ or $AS_{END}$. Rather, the device senses an atrial event based on the amplitude of the event exceeding some detection threshold. Hence, $AS$-$VP_{PULSE}^{INITIAL}$ is simply the interval between the point where the atrial event exceeds the threshold to the $V_{PULSE}$.) At step 214, the device detects the peaks of ventricular evoked responses triggered by the $V_{PULSES}$ and, at step 216, measures the average observed time delay between the ends of the atrial depolarizations and the peaks of the ventricular evoked responses, which is referred to herein as $AS_{END}$-$VP_{PEAK}^{OBSERVED}$. At step 218, the optimization system then calculates the preferred AV pacing delay for use with sensed atrial events using the following equation:

is triggered by a $V_{PULSE}$ 226. Exemplary time delay values for $AS$-$V_{PULSE}^{INITIAL}$, $AS_{END}$-$VP_{PEAK}^{PREFERRED}$, and $AS_{END}$-$VP_{PEAK}^{OBSERVED}$ are also illustrated. As can be seen, there is a substantial difference between the preferred time delay to be achieved ($AS_{END}$-$VP_{PEAK}^{PREFERRED}$) and the actual time delay that is observed ($AS_{END}$-$VP_{PEAK}^{OBSERVED}$) when using the initial, arbitrarily-selected delay value $AS$-$V_{PULSE}^{INITIAL}$. The features of timing diagram 218, and the features of other timing diagrams described herein, are not necessarily drawn to scale.

Figure 3:
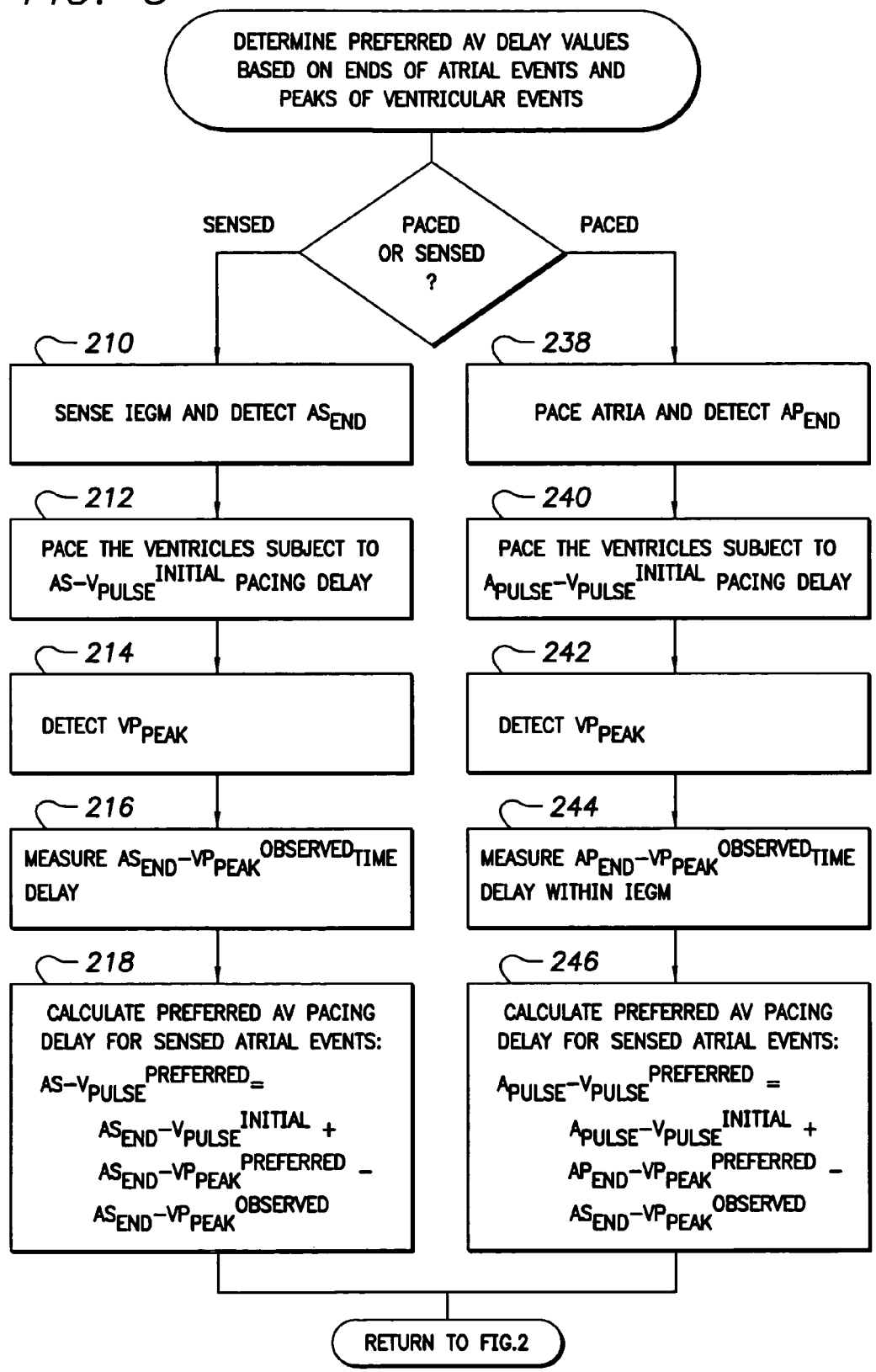
FIG. 3 is a flow chart illustrating a specific technique for determining preferred AV pacing delay values for paced and sensed events for use with the technique of FIG. 2, which seeks to achieve a preferred time delay specified between the ends of atrial events and the peaks of ventricular events with an IEGM signal.

In contrast, timing diagram 228 illustrates the IEGM when the patient is instead paced using the preferred AV pacing delay (i.e. $AS$-$V_{PULSE}^{PREFERRED}$) calculated at step 218 and FIG. 3. Again, an atrial depolarization 230, ventricle evoked response 232 and ventricular repolarization 234 are illustrated, along with a $V_{PULSE}$ 236. When paced using the $AS$-$V_{PULSE}^{PREFERRED}$ delay value, the new observed time delay from the end of the atrial event to the peak of the ventricular evoked response (referred to as $AS_{END}$-$VP_{PEAK}^{NEW}$) now matches the preferred time delay ($AS_{END}$-$VP_{PEAK}^{PREFERRED}$.) In other words, by using the preferred time delay value calculated at step 218 of FIG. 3, the preferred time delay (specified between the end of the atrial depolarization and the peak of the subsequent ventricular evoked response) is thereby achieved so as to achieve improved cardiac function.

Returning to FIG. 3, the processing of paced atrial events will now be described. Many of these steps are similar to the corresponding sensed event processing steps already discussed and hence will only be summarized. Beginning at step 238, the implantable device paces the atria of the patient using $A_{PULSES}$, detects the resulting atrial evoked responses (AP) and identifies the ends thereof ($AP_{END}$). At step 240, the device then delivers $V_{PULSES}$ to the ventricles at times specified by $A_{PULSE}$-$V_{PULSE}^{INITIAL}$.) At step 242, the device detects the peaks of the ventricular evoked responses and, at step 244, measures the average observed time delay between the ends of the atrial evoked responses and the peaks of the ventricular evoked responses, which is referred to herein as $AP_{END}$-$VP_{PEAK}^{OBSERVED}$. At step 246, the optimization sys- $$AS\text{-}V_{PULSE}^{PREFERRED} = AS\text{-}V_{PULSE}^{INITIAL} + AS_{END}\text{-}VP_{PEAK}^{PREFERRED} - AS_{END}\text{-}VP_{PEAK}^{OBSERVED}.$$

Processing then returns to FIG. 2 where $AS_{END}$-$V_{PULSE}^{PREFERRED}$ is adjusted based upon the current intrintem then calculates the preferred AV pacing delay for use with paced atrial events using the following equation:

$$A_{PULSE}\text{-}V_{PULSE}^{PREFERRED} = A_{PULSE}\text{-}V_{PULSE}^{INITIAL} + AP_{END}\text{-}VP_{PEAK}^{PREFERRED} - AP_{END}\text{-}VP_{PEAK}^{OBSERVED}$$

sic rate of the patient then employed for subsequent AV pacing following atrial sensed events.

Figure 4:
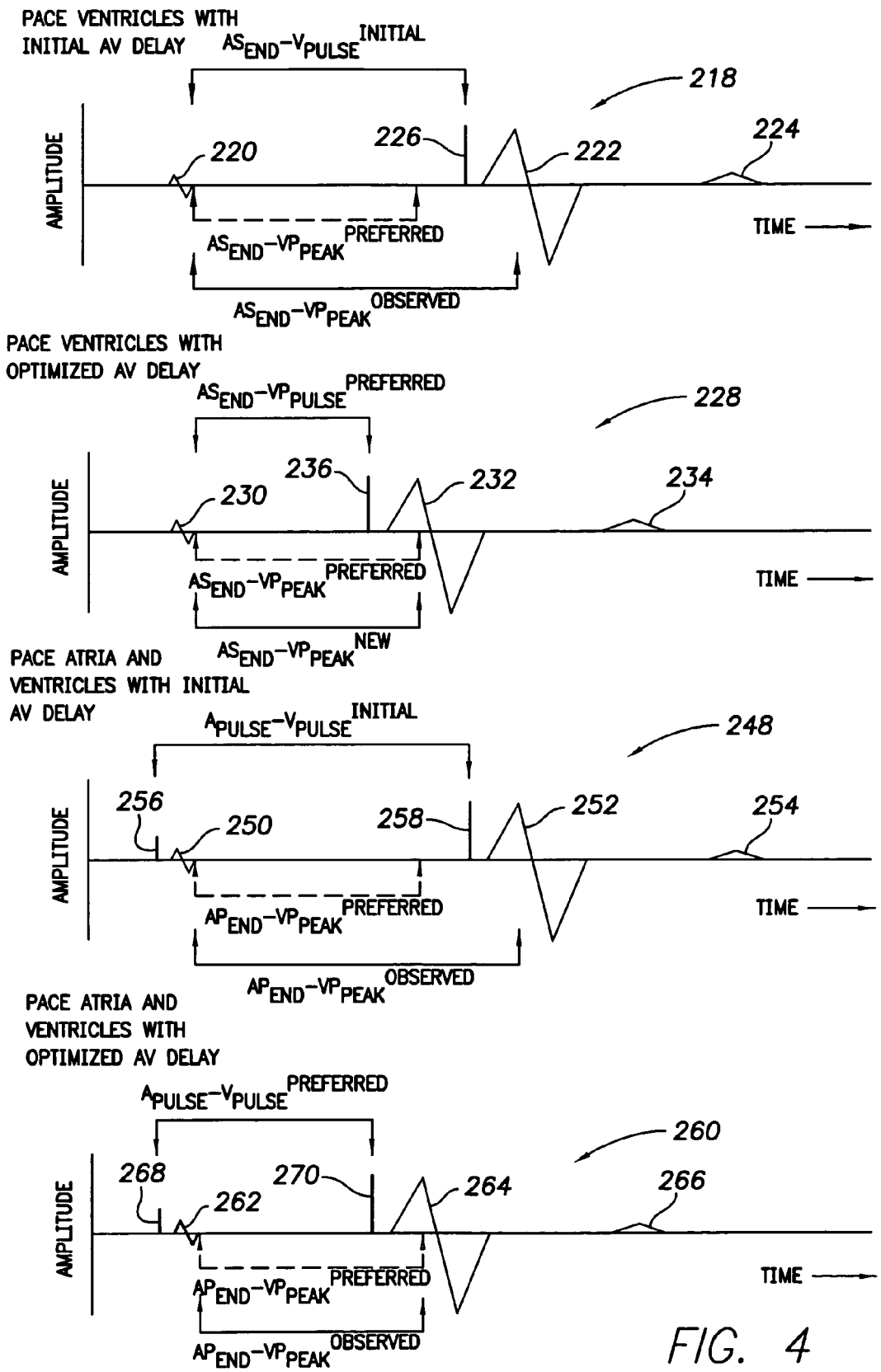
FIG. 4 provides a set of graphs illustrating time delay values employed by the technique of FIG. 3.

FIG. 4 provides stylized, exemplary IEGM timing diagrams that illustrate the various time delay values employed by the technique of FIG. 3. Referring first to timing diagram 218 of FIG. 4, an atrial depolarization 220, a ventricular evoked response 222 and a ventricular repolarization 224 are shown for a single heartbeat. The ventricular evoked response Processing then returns to FIG. 2 where the $A_{PULSE}$-$V_{PULSE}^{PREFERRED}$ is adjusted based upon the current pacing rate of the patient, then employed for subsequent AV pacing following atrial pulses.

Referring now to the third timing diagram 248 of FIG. 4, an atrial evoked response 250, a ventricular evoked response 252 and a ventricular repolarization 254 are shown for a single heartbeat. The atrial evoked response is triggered by an $A_{PULSE}$ 256. The ventricular evoked response is triggered by a $V_{PULSE}$ 258. Exemplary time delay values for $A_{PULSE}$-$V_{PULSE}^{INITIAL}$, $AP_{END}$-$VP_{PEAK}^{PREFERRED}$, and $AP_{END}$-$VP_{PEAK}^{OBSERVED}$ are also illustrated. There is a substantial difference between the preferred time delay to be achieved ($AP_{END}$-$VP_{PEAK}^{PREFERRED}$) and the actual time delay that is observed ($AP_{END}$-$VP_{PEAK}^{OBSERVED}$) when using the initial, arbitrarily-selected delay value $A_{PULSE}$-$V_{PULSE}^{INITIAL}$.

In contrast, timing diagram 260 illustrates the IEGM when the patient is instead paced using the preferred AV pacing delay (i.e. $A_{PULSE}$-$V_{PULSE}^{PREFERRED}$) calculated at step 246 and FIG. 3. Again, an atrial evoked response 262, ventricle evoked response 264 and ventricular repolarization 266 are illustrated, along with an $A_{PULSE}$ 268 and $V_{PULSE}$ 270. When paced using the $A_{PULSE}$-$V_{PULSE}^{PREFERRED}$ delay value, the new observed time delay from the end of the atrial evoked response to the peak of the ventricular evoked response (referred to herein as $AP_{END}$-$VP_{PEAK}^{NEW}$) now matches the preferred time delay ($AP_{END}$-$VP_{PEAK}^{PREFFERED}$.) Thus, by using the preferred time delay value calculated at step 246 of FIG. 3, the preferred time delay between specified between the end of the atrial evoked response and the peak of the subsequent ventricular evoked response is thereby achieved so as to improve cardiac function.

Hence, upon completion of the steps of FIGS. 3-4, the implantable device has calculated preferred AV pacing delay values for use with both paced and sensed atrial events.

As noted, in an implementation wherein the IEGM signals being processed are unipolar RAT-case signals, the preferred delay values ($AS_{END}$-$VP_{PEAK}^{PREFERRED}$ and $AP_{END}$-$VP_{PEAK}^{PREFERRED}$) are both set to 100 ms. This value is derived from studies, discussed in the Strohmer et al. reference cited above, indicating that the optimal time delay between the end of a P-wave and the peak of an R-wave within a surface EKG is 100 ms. The value appears to provide a physiological, age-adjusted standard value for effective left heart AV-synchrony. Accordingly, by setting $AS_{END}$-$VP_{PEAK}^{PREFERRED}$ and $AP_{END}$-$VP_{PEAK}^{PREFERRED}$ to 100 ms, it is believed that the resulting AV pacing delay values ($AS_{END}$-$V_{PULSE}^{PREFERRED}$ and $A_{PULSE}$-$V_{PULSE}^{PREFERRED}$) determined by the invention will achieve fairly effective AV-synchrony as well and hence represent preferred values. However, by sensing the IEGM via unipolar RAT-case signals, the sensing of atrial events is local, whereas the sensing of ventricular events is global. Accordingly, although $VP_{PEAK}$ observed within the IEGM will be substantially contemporaneous with the peak of the R-wave in a corresponding surface EKG, there may be an offset between the ends of atrial events within the IEGM and the end of the corresponding P-wave of the EKG. In other words, 100 ms may not be the true optimal delay value for use with unipolar RAT-case signals. If this offset is significant, the calibration techniques of FIGS. 6-8 may be used to adjust for the offset. If the offset is relatively small, perhaps 5-10 ms or less, than no calibration is typically needed.

If a different pair of electrodes are selected for sensing the IEGM signal instead of RAT and case, then it may be desirable to specify different preferred delay values (other than 100 ms) and/or use different calibration offset values. If a different pair of morphological features are selected (other than the ends of the atrial events and the peaks of ventricular events), then care should be taken in selecting the preferred delay values (i.e. $AS$-$VP^{PREFERRED}$ and $AP$-$VP^{PREFERRED}$) for use with those features. For example, if the beginning of the atrial event is selected for timing delays rather than the end, it may be appropriate to add the average width of the atrial event to the aforementioned 100 ms delay value to provide a preferred value for use as $AS_{BEGINNING}$-$VP_{PEAK}^{PREFERRED}$. Clinical studies may be useful in some cases to identify optimal delay values for use between selected pairs of features. In some cases, adjustments may be desirable based on age, gender, or the like. As can be appreciated, a wide variety of specific implementations are consistent with the invention. Those of ordinary skill in the art, using the principles of the invention described herein, may derive suitable preferred delay values for use in different implementations without undue experimentation.

Exemplary Adjustment Technique Based on Intrinsic Rate or Pacing Rate

Figure 5:
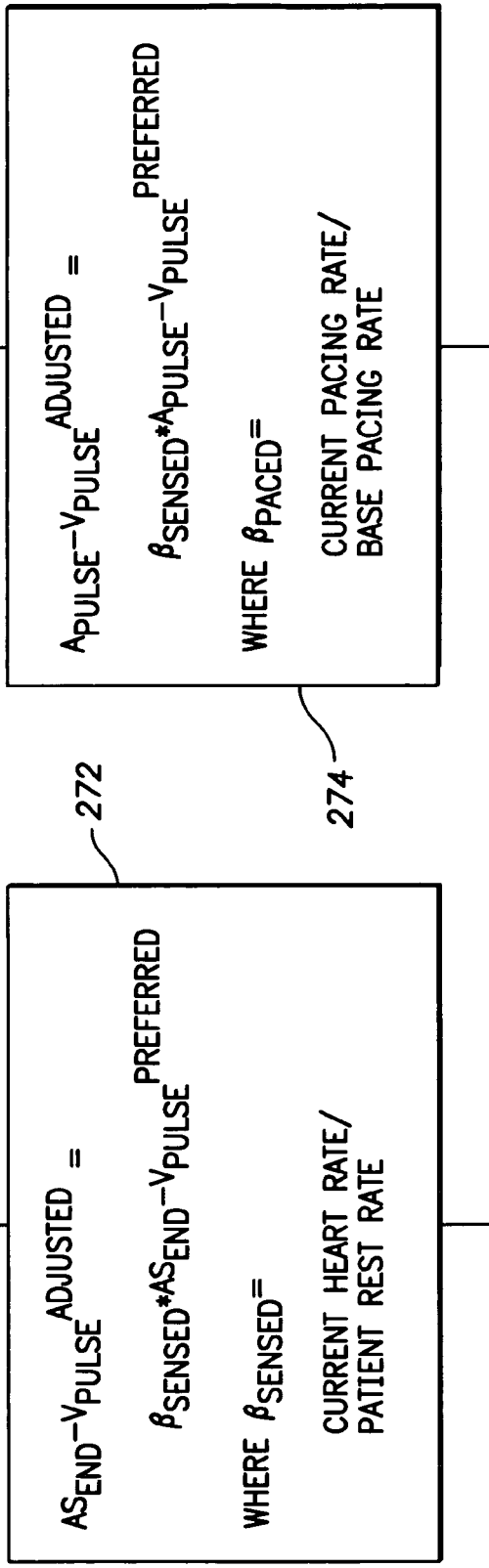
FIG. 5 is a flow chart illustrating an exemplary technique for adjusting preferred AV pacing delay values based on heart rate or pacing rate for use with the technique of FIG. 2.

For pacing rates that are not at the base pacing rate programmed for the patient or for intrinsic heart rates that are not at the patient rest rate, the preferred AV pacing delay values are automatically adjusted by the implantable device that step 206 of FIG. 2 using the technique FIG. 5. Again, the particular steps to be performed depend upon whether atrial events are paced or sensed. For sensed atrial events, step 272 is performed, wherein $AS_{END}$-$V_{PULSE}^{PREFERRED}$ is adjusted as follows:

$$AS_{END}\text{-}V_{PULSE}^{ADJUSTED} = \beta_{SENSED} * AS_{END}\text{-}V_{PULSE}^{PREFERRED}$$

where $\beta_{SENSED}$ = Current Heart Rate/Patient Rest Rate.

For paced events in the atria, $A_{PULSE}$-$V_{PULSE}^{PREFERRED}$ is adjusted, at step 274, as follows:

$$A_{PULSE}\text{-}V_{PULSE}^{ADJUSTED} = \beta_{PACED} * A_{PULSE}\text{-}V_{PULSE}^{PREFERRED}$$

where $\beta_{PACED}$ = Current Pacing Rate/Base Pacing Rate.

The Current Heart Rate of the patient is determined by the implantable device in accordance with otherwise conventional techniques. The Base Pacing Rate is a programmable value.

Exemplary Optimization Technique Using Calibration Offset Values

Figure 6:
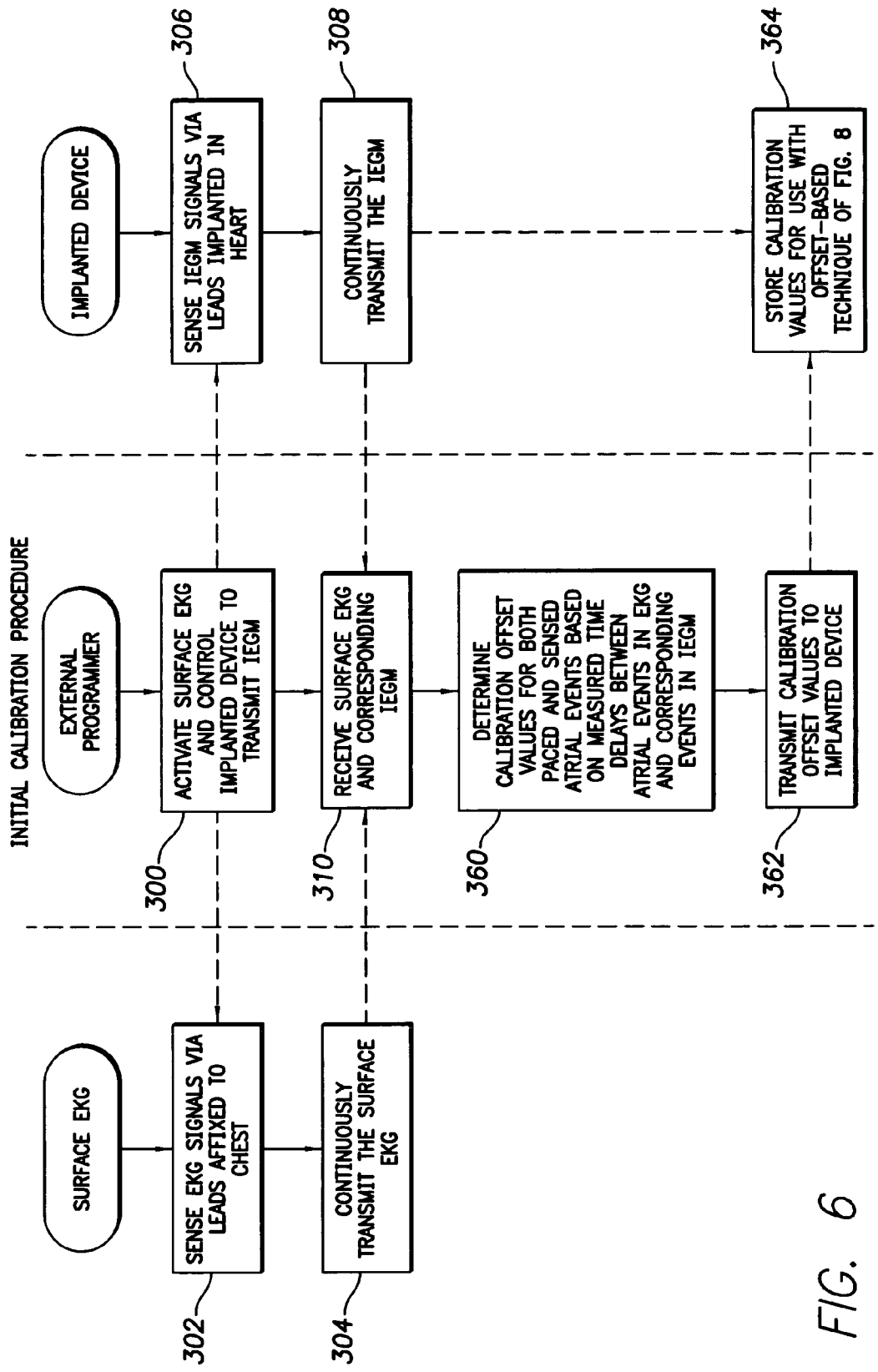
FIG. 6 is a flow chart illustrating an initial calibration procedure for determining offset values for use with an alternate implementation of the technique of FIG. 2.
Figure 8:
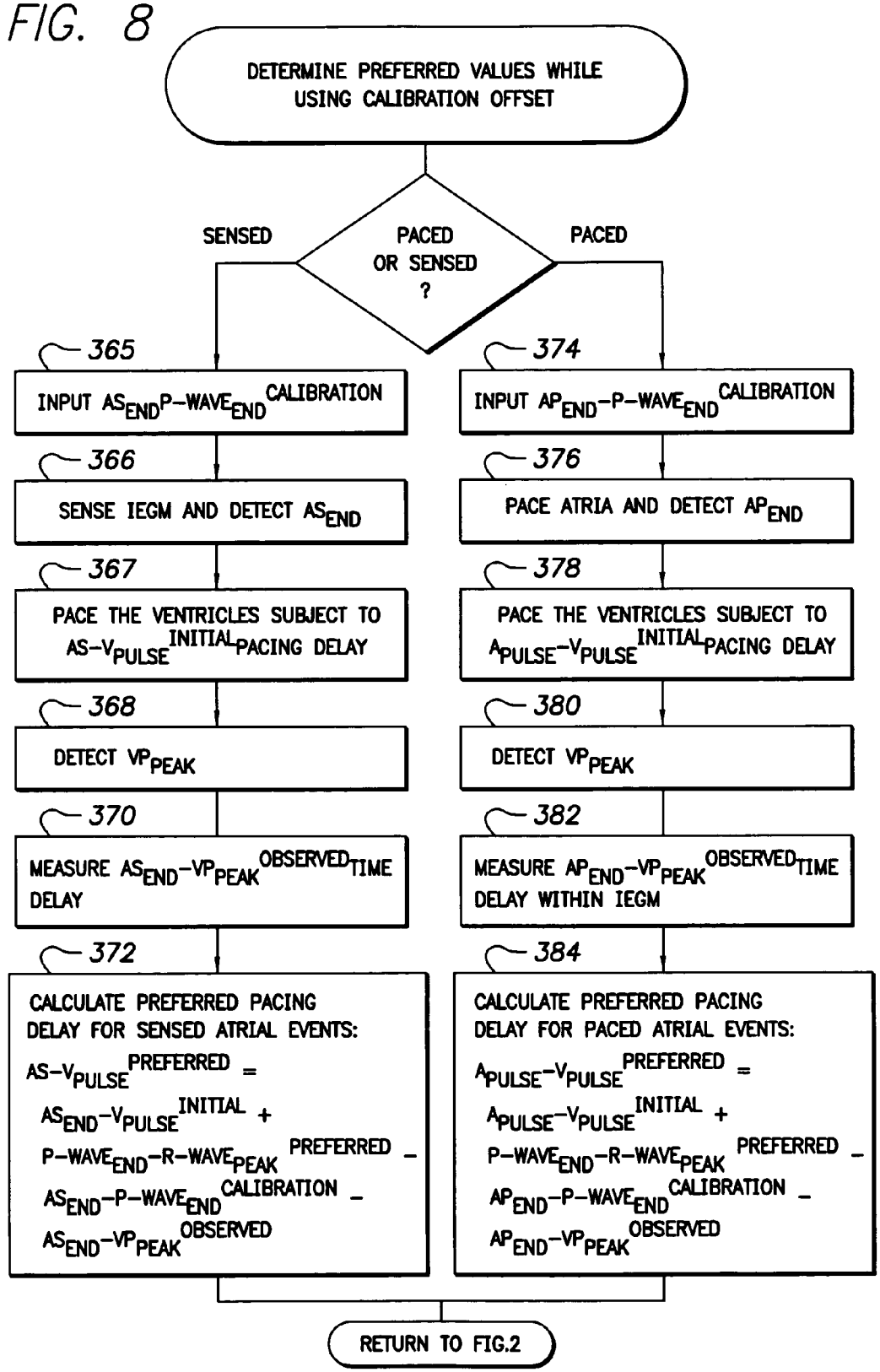
FIG. 8 is a flow chart illustrating an alternative technique for determining preferred AV pacing delay values for paced and sensed events for use with the technique of FIG. 2, which employs the offset values calculated via FIG. 6.

Turning now to FIGS. 6-8, an alternative optimization technique will now be described, which employs an initial calibration procedure. Whereas the techniques set forth above specify the time delay values to be achieved (i.e. $AS_{END}$-$VP_{PEAK}^{PREFERRED}$ and $AP_{END}$-$VP_{PEAK}^{PREFERRED}$) in terms of features of the IEGM, with the techniques of FIGS. 6-8, the time delay values to be achieved are instead specified in terms of features of a surface EKG. Accordingly, to apply the optimization technique within an implantable device based on IEGM signals, a calibration offset value is calculated in advance for use in compensating for timing differences between the surface EKG and the IEGM signals. The initial calibration procedure will be described first with reference to FIGS. 6-7, then an AV pacing delay optimization procedure that uses the resulting calibration offset values will be described with reference to FIG. 8.

FIG. 6 summarizes the initial calibration procedure, which is performed by an external device programmer while in communication with the implanted device and a surface EKG system. Steps performed by the surface EKG system are shown on the left; steps performed by the external programmer are shown in the center; and steps performed by the implanted device are shown on the right. Initially, at step 300, the external programmer activates the surface EKG system to detect EKG signals representative of the electrical cardiac activity of a patient via leads affixed to the chest of the patient.

At step 300, the programmer also controls the implanted device (via control signals transmitted, e.g., via a telemetry wand) to transmit IEGM signals back to the programmer. The surface EKG is detected at step 302 and output from the surface EKG system to the programmer at step 304. Meanwhile, the implanted device senses IEGM signals at step 306 and transmits the signals to the programmer at step 308. The various signals are received by the programmer at step 310. The programmer thereby receives contemporaneous surface EKG and IEGM signals both representative of the same electrical cardiac activity within the patient. Although the surface EKG and the IEGM both represent the same the electrical cardiac activity of the patient, there are nevertheless differences in the signal patterns due to the differing locations of the electrodes used to detect the electrical signals.

FIG. 7 illustrates differences between the surface EKG and a unipolar RAT-case IEGM by way of exemplary, stylized timing diagrams. A first timing diagram 312 illustrates an IEGM pattern for a single heartbeat wherein the atria beat intrinsically but the ventricles are paced. The heartbeat includes an atrial depolarization 314, a ventricular evoked response 316 and a ventricular repolarization 318. The ventricular evoked response is triggered by a $V_{PULSE}$ 320. A second timing diagram 322 illustrates the corresponding surface EKG, which includes a P-wave 324, an R-wave 326, and a T-wave 328. The $V_{PULSE}$ is represented within the surface EKG by a voltage spike 330. As can be seen, the features of the surface EKG differ in shape and timing from the corresponding features of the IEGM. In particular, because the IEGM is a local signal sensed RAT-case whereas the surface EKG is a global signal, an end of the P-wave of the surface EKG is delayed relative to the end of the corresponding atrial depolarization within the IEGM. The external programmer measures this offset, which is referred to herein as $AS_{END}$-P-WAVE$_{END}^{CALIBRATION}$. Note that the peak of the R-wave of the EKG and the peak of the ventricular evoked response of the IEGM are substantially aligned and so a $VP_{PEAK}$-R-WAVE$_{PEAK}^{CALIBRATION}$ value is not required.

A third timing diagram 336 illustrates an IEGM pattern for a single heartbeat wherein both the atria and the ventricles are paced. The heartbeat includes an atrial evoked response 338, a ventricular evoked response 340 and a ventricular repolarization 342. The atrial evoked response is triggered by an $A_{PULSE}$ 344. The ventricular evoked response is triggered by a $V_{PULSE}$ 346. A fourth timing diagram 348 illustrates the corresponding surface EKG, which includes a P-wave 350, an R-wave 352, and a T-wave 354. The $A_{PULSE}$ and the $V_{PULSE}$ are represented with in the surface EKG by voltage spikes 356 and 358, respectively. Again, an end of the P-wave of the surface EKG is delayed relative to the end of the corresponding atrial evoked response within the IEGM. The external programmer measures this offset, which is referred to herein as $AP_{END}$-P-WAVE$_{END}^{CALIBRATION}$. $AP_{END}$-P-WAVE$_{END}^{CALIBRATION}$ and $AS_{END}$-P-WAVE$_{END}^{CALIBRATION}$ are typically quite similar and so, in many cases, only a single one of the values may need to be calculated (referred to generally as $A_{END}$-P-WAVE$_{END}^{CALIBRATION}$.) The use of both is described herein for the sake of completeness.

Returning to FIG. 6, the external programmer, at step 360, determines the time delays between the ends of atrial events in the IEGM and the ends of P-waves in the surface EKG, i.e. the external programmer calculates the aforementioned $AP_{END}$-P-WAVE$_{END}^{CALIBRATION}$ and $AS_{END}$-P-WAVE$_{END}^{CALIBRATION}$ values. Preferably, these values are averaged over some suitable number of heartbeats or over some suitable period of time. In any case, at step 362, the values are transmitted to the implanted device, which receives the values at step 364 and stores them within internal memory and for subsequent use in connection with the offset-based optimization technique of a FIG. 8.

Turning now to FIG. 8, the optimization technique that uses the calibration offset values will now be described. This technique is used when the preferred delay values to be achieved are specified in terms of features of the surface EKG rather than the IEGM. In the example of FIG. 8, a single preferred delay value for use with either paced or sensed atrial events is specified between the end of P-waves and the peaks of R-waves within the surface EKG. The value is referred to herein as P-WAVE$_{END}$-R-wave$_{PEAK}^{PREFERRED}$. Accordingly, the calibration offset values are used to adjust of any timing difference between the ends of atrial events in the IEGM and the ends of P-waves in the surface EKG. Note that many of the steps of FIG. 8 are similar to corresponding steps of FIG. 3 and will not be described again in detail. Steps performed based on atrial sensed events are again shown on the left; whereas steps performed based on paced atrial events are shown on the right.

Beginning at step 365, the optimization system retrieves the $AS_{END}$-P-WAVE$_{END}^{CALIBRATION}$ value from internal memory, which had been previously calculated by the external programmer then stored within the implantable device. At step 366, the implantable device detects intrinsic atrial depolarizations and identifies $AS_{END}$ and then, at step 367, paces the ventricles at times specified by AS–$V_{PULSE}^{INITIAL}$. At step 368, the device detects $VP_{PEAK}$ values and, at step 370, measures $AS_{END}$–$VP_{PEAK}^{OBSERVED}$. At step 372, the optimization system then calculates the preferred AV pacing delay for use with sensed atrial events using the following equation:

$$AS\text{-}V_{PULSE}^{PREFERRED} = AS\text{-}V_{PULSE}^{INITIAL} + P\text{-}WAVE_{END}\text{-}R\text{-}WAVE_{PEAK}^{PREFERRED} - AS_{END}\text{-}P\text{-}WAVE_{END}^{CALIBRATION} - AS_{END}\text{-}VP_{PEAK}^{OBSERVED}.$$

The processing of paced atrial events will now be summarized. Beginning at step 374, the optimization system retrieves the $AP_{END}$-P-WAVE$_{END}^{CALIBRATION}$ value from internal memory and, at step 376, begins pacing the atria and detecting $AP_{END}$ values. At step 378, the device then paces the ventricles at times specified by $A_{PULSE}$–$V_{PULSE}^{INITIAL}$. At step 380, the device detects $VP_{PEAK}$ values and, at step 382, measures $AP_{END}$–$VP_{PEAK}^{OBSERVED}$. At step 384, the optimization system then calculates the preferred AV pacing delay for use with paced atrial events using the following equation:

$$A_{PULSE}\text{-}V_{PULSE}^{PREFERRED} = A_{PULSE}\text{-}V_{PULSE}^{INITIAL} + P\text{-}WAVE_{END}\text{-}R\text{-}WAVE_{PEAK}^{PREFERRED} -$$
$$AP_{END}\text{-}P\text{-}WAVE_{END}^{CALIBRATION} - AP_{END}\text{-}VP_{PEAK}^{OBSERVED}.$$

By taking into account the calibration factors, the average observed time delay values are thereby adjusted so as to conform to the preferred delay value specified in terms of features of the surface EKG (i.e. P-WAVE$_{END}$-R-WAVE$_{PEAK}^{PREFERRED}$.) Processing then returns to FIG. 2 where the preferred AV pacing delay values are adjusted based upon the current intrinsic rate of the patient or the pacing rate and then employed for subsequent AV pacing.

Note that techniques have been developed for emulating a surface EKG using internal electrical cardiac signals. See, for example, U.S. patent application Ser. No. 10/735,948 of Kil et al., filed Dec. 12, 2003, entitled "System and Method for Emulating a Surface EKG Using Internal Cardiac Signals Sensed by an Implantable Medical Device" which is incorporated by reference herein. See also, U.S. patent application Ser. No. 10/334,741 to Kroll et al., entitled "System and Method for Emulating a Surface EKG Using Implantable Cardiac Stimulation Device," filed Dec. 30, 2002, which is also incorporated by reference herein. If the implanted device is capable of reliably emulating a surface EKG, then it may be feasible to determine the calibration offset values based on a comparison of the IEGM and the emulated EKG, thereby eliminating the need for performing the initial calibration using an actual surface EKG.

What have been described thus far are various techniques for determining preferred or optimal AV pacing delay values for use by an implantable medical device. While described with respect to certain exemplary IEGM configuration, other IEGM configurations—such as various unipolar and bipolar IEGM configurations from various leads (RV, LV)—are applicable to this method as well. Depending upon the implementation, the determination techniques are performed by the implanted device exclusively or by the implanted device using calibration offset values originally calculated by an external programmer. For the sake of completeness, detailed descriptions of exemplary implantable medical devices and external programmers will now be described.

Exemplary Pacer/ICD

Figure 9:
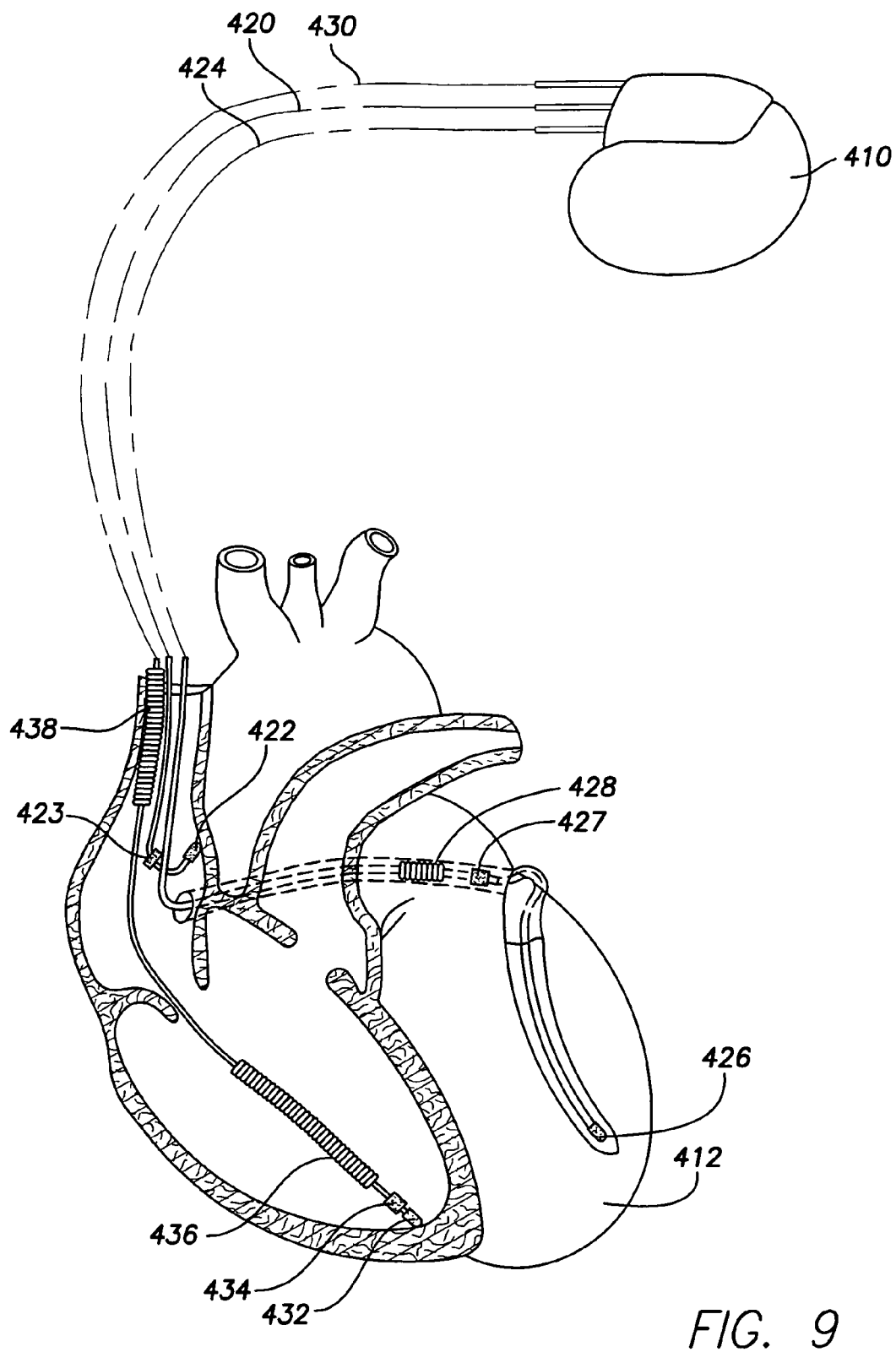
FIG. 9 is a simplified diagram illustrating an implantable stimulation device for use in implementing techniques of FIGS. 1-8.
Figure 10:
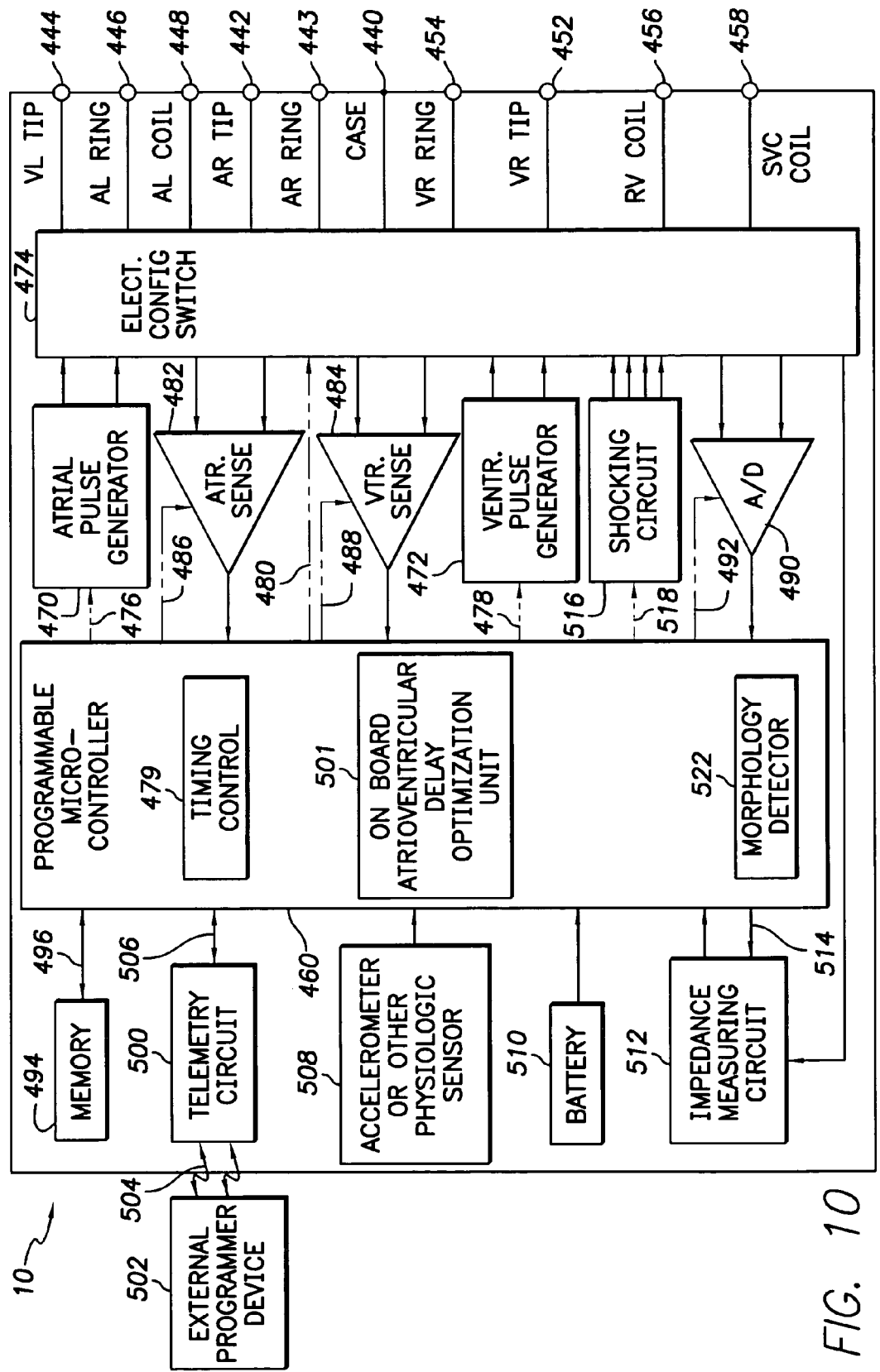
FIG. 10 is a functional block diagram of internal components of the implantable device of FIG. 9.

With reference to FIGS. 9 and 10, a description of an exemplary pacer/ICD will now be provided. FIG. 9 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 9, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 410 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/CD 410, shown schematically in FIG. 10, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal (A$_R$ TIP) 442 adapted for connection to the atrial tip electrode 422 and a right atrial ring (A$_R$ RING) electrode 443 adapted for connection to right atrial ring electrode 423. To achieve left chamber sensing, pacing and shocking, the connector includes at least a left ventricular tip terminal (V$_L$ TIP) 444, a left atrial ring terminal (A$_L$ RING) 446, and a left atrial shocking terminal (A$_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal (V$_R$ TIP) 452, a right ventricular ring terminal (V$_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 10, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, AV delay, atrial interconduction (inter-atrial) delay, or ventricular interconduction (V–V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV delay, V–V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

Insofar as AV delay values are concerned, the microcontroller includes an on-board AV pacing delay optimization unit 501, which operates in accordance with any of the techniques of FIGS. 1-8 to determine preferred or optimal $AS-V_{PULSE}$ and $A_{PULSE}-V_{PULSE}$ delay values based on IEGM signals.

The pacer/ICD additionally includes a battery 510, which provides operating power to all of the circuits shown in FIG. 10. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 10, pacer/ICD 410 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Exemplary External Programmer

Figure 11:
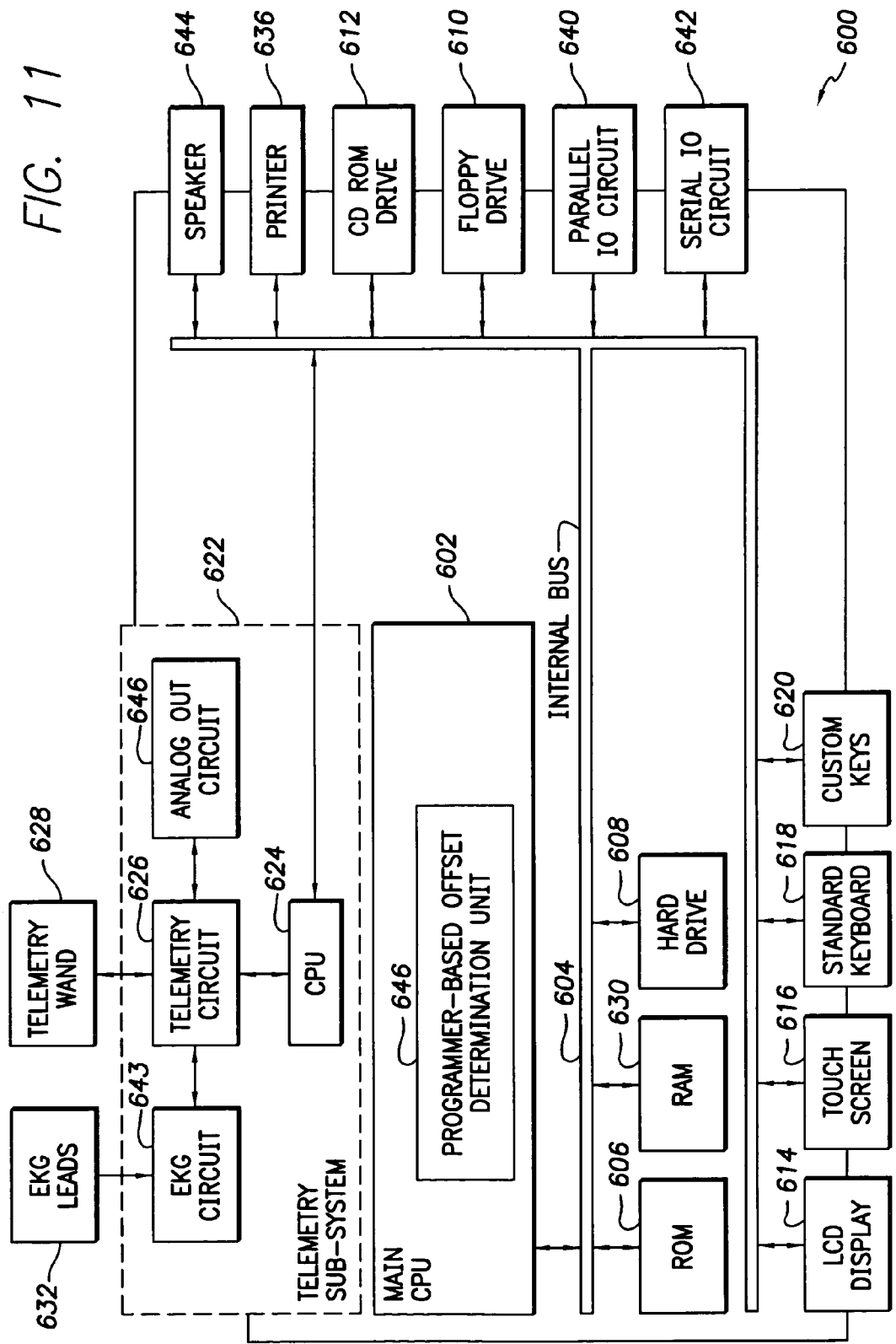
FIG. 11 is a functional block diagram of an external programmer device for use in implementing the initial calibration step of FIG. 6.

FIG. 11 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays EKG data from separate external EKG leads that may be attached to the patient. Depending upon the specific programming of the external programmer, programmer 600 may also be capable of processing and analyzing data received from the implanted device and from the EKG leads to, for example, render preliminary diagnosis as to medical conditions of the patient or to the operations of the implanted device. As noted, the programmer is also configured to determination preferred or optimal $AS-V_{PULSE}$ and AP–VP delay values.

Now, considering the components of programmer 600, operations of the programmer are controlled by a CPU 602, which may be a generally programmable microprocessor or microcontroller or may be a dedicated processing device such as an application specific integrated circuit (ASIC) or the like. Software instructions to be performed by the CPU are accessed via an internal bus 604 from a read only memory (ROM) 606 and random access memory 630. Additional software may be accessed from a hard drive 608, floppy drive 610, and CD ROM drive 612, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 614 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 616 overlaid on the LCD display or through a standard keyboard 618 supplemented by additional custom keys 620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various devices are programmed. Typically, the physician initially controls the programmer 600 to retrieve data stored within any implanted devices and to also retrieve EKG data from EKG leads, if any, coupled to the patient. To this end, CPU 602 transmits appropriate signals to a telemetry subsystem 622, which provides components for directly interfacing with the implanted devices, and the EKG leads. Telemetry subsystem 622 includes its own separate CPU 624 for coordinating the operations of the telemetry subsystem. Main CPU 602 of programmer communicates with telemetry subsystem CPU 624 via internal bus 604. Telemetry subsystem additionally includes a telemetry circuit 626 connected to telemetry wand 628, which, in turn, receives and transmits signals electromagnetically from a telemetry unit of the implanted device. The telemetry wand is placed over the chest of the patient near the implanted device to permit reliable transmission of data between the telemetry wand and the implanted device.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted devices is stored by external programmer 600 either within a random access memory (RAM) 630, hard drive 608 or within a floppy diskette placed within floppy drive 610. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 600, the implanted devices may be further controlled to transmit additional data in real time as it is detected by the implanted devices, such as additional IEGM data, lead impedance data, and the like. Additionally, or in the alternative, telemetry subsystem 622 receives EKG signals from EKG leads 632 via an EKG processing circuit 634. As with data retrieved from the implanted device itself, signals received from the EKG leads are stored within one or more of the storage devices of the external programmer. Typically, EKG leads output analog electrical signals representative of the EKG. Accordingly, EKG circuit 634 includes analog to digital conversion circuitry for converting the signals to digital data appropriate for further processing within programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from the external EKG leads. Data retrieved from the implanted devices includes parameters representative of the current programming state of the implanted devices. Under the control of the physician, the external programmer displays the current programming parameters and permits the physician to reprogram the parameters. To this end, the physician enters appropriate commands via any of the aforementioned input devices and, under control of CPU 602, the programming commands are converted to specific programming parameters for transmission to the implanted devices via telemetry wand 628 to thereby reprogram the implanted devices. Prior to reprogramming specific parameters, the physician may control the external programmer to display any or all of the data retrieved from the implanted devices or from the EKG leads, including displays of ECGs, IEGMs, and statistical patient information. Any or all of the information displayed by programmer may also be printed using a printer 636.

A wide variety of parameters may be programmed by the physician. Insofar as the aforementioned calibration offset values are concerned, the microcontroller includes a programmer-based offset determination unit 646, which operates in accordance with technique of FIG. 6 to determine initial offset values (i.e. $AS_{END}$–P-WAVE$_{END}^{CALIBRATION}$ and $AP_{END}$–P-WAVE$_{END}^{CALIBRATION}$) during an initial calibration step based on surface EKG signals and IEGM signals received from an implanted device. The offset values are transmitted to the implanted device for use therein.

Programmer 600 also includes a modem 638 to permit direct transmission of data to other programmers via the public switched telephone network (PSTN) or other interconnection line, such as a T1 line or fiber optic cable. Depending upon the implementation, the modem may be connected directly to internal bus 604 may be connected to the internal bus via either a parallel port 640 or a serial port 642. Other peripheral devices may be connected to the external programmer via parallel port 640 or a serial port 642 as well. Although one of each is shown, a plurality of input output (IO) ports might be provided. A speaker 644 is included for providing audible tones to the user, such as a warning beep in the event improper input is provided by the physician. Telemetry subsystem 622 additionally includes an analog output circuit 646 for controlling the transmission of analog output signals, such as IEGM signals output to an EKG machine or chart recorder.

With the programmer configured as shown, a physician or other user operating the external programmer is capable of retrieving, processing and displaying a wide range of information received from the EKG leads or from the implanted devices and to reprogram the implanted devices if needed. The descriptions provided herein with respect to FIG. 11 are intended merely to provide an overview of the operation of programmer and are not intended to describe in detail every feature of the hardware and software of the device and is not intended to provide an exhaustive list of the functions performed by the device.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use by an implantable medical device for determining a preferred atrioventricular (AV) delay pacing value for use in delivering cardiac pacing therapy to the heart of a patient in which the device is implanted, the method comprising:
pacing the heart using an initial AV pacing delay set to a value less than an intrinsic AV conduction delay;
sensing an internal electrical cardiac signal between an atrial tip electrode and a case of the implantable device and identifying an atrial event and a subsequent paced ventricular event therein;
measuring a time delay between the atrial event and the subsequent paced ventricular event; and
determining the preferred AV pacing delay value based on the initial AV pacing delay, the measured time delay between the atrial event and the subsequent paced ventricular event, and on a predetermined preferred time delay to be achieved between atrial events and subsequent paced ventricular events.

2. The method of claim 1 performed to determine a preferred AV pacing delay value for use in pacing the ventricles subsequent to an intrinsic atrial depolarization (i.e. $AS\text{-}V_{PULSE}^{PREFERRED}$).

3. The method of claim 2 wherein the step of determining the preferred AV pacing delay value for use in pacing the ventricles subsequent to an intrinsic atrial depolarization includes calculating:

$$AS\text{-}V_{PULSE}^{PREFERRED}=AS\text{-}V_{PULSE}^{INITIAL}+AS\text{-}VP^{PREERRED}-AS\text{-}VP^{OBSERVED}$$

wherein $AS\text{-}V_{PULSE}^{INITIAL}$ is a predetermined initial AV delay for use with paced atrial events, $AS\text{-}VP^{PREFERRED}$ is a predetermined preferred delay value for use with sensed atrial events, $AS\text{-}VP^{OBSERVED}$ is the measured delay value and $AS\text{-}V_{PULSE}^{PREFERRED}$ is the resulting preferred AV pacing delay value.

4. The method of claim 3 wherein the method includes the step of adjusting $AS\text{-}VP^{OBSERVED}$ using a calibration offset value input to the device that is representative of an average time delay between sensed atrial events as observed within internal cardiac signals and corresponding P-waves as observed within a surface electrocardiogram (EKG).

5. The method of claim 2
wherein the step of measuring the time delay between the sensed atrial event and the corresponding paced ventricular event is performed to measure the time delay between a selected feature of the sensed atrial event and a selected feature of the paced ventricular event, and
wherein the predetermined preferred time delay between atrial events and subsequent paced ventricular events is specified based on the same selected features.

6. The method of claim 5 wherein the selected features are selected from a group including beginning, peak, and end.

7. The method of claim 2 wherein the step of determining the preferred AV pacing delay value for use in pacing the ventricles subsequent to an intrinsic atrial depolarization includes calculating:

$$AS\text{-}V_{PULSE}^{PREFERRED}=AS\text{-}V_{PULSE}^{INITIAL}+AS_{END}\text{-}VP_{PEAK}^{PREFERRED}-AS_{END}\text{-}VP_{PEAK}^{OBSERVED}$$

wherein $AS\text{-}V_{PULSE}^{INITIAL}$ is a predetermined initial AV delay between the end of sensed atrial events and the $V_{PULSES}$, $AS_{END}\text{-}VP_{PEAK}^{PREFERRED}$ is a predetermined preferred delay value between the end of sensed atrial events and the peaks of subsequent paced ventricular events, $AS_{END}\text{-}VP_{PEAK}^{OBSERVED}$ is the measured delay value between the end of a sensed atrial event and the peak of the subsequent paced ventricular event, and $AS\text{-}V_{PULSE}^{PREFERRED}$ is the resulting preferred AV pacing delay value.

8. The method of claim 7 wherein $AS_{END}\text{-}VP_{PEAK}^{PREFERRED}$ is in the range of 95 milliseconds (ms) to 105 ms.

9. The method of claim 7 wherein the internal electrical cardiac signals are sensed between an atrial tip electrode and a case of the implantable device and wherein the method includes the initial step of adjusting $AS_{END}\text{-}VP_{PEAK}^{OBSERVED}$ using on an offset value input to the device that is representative of an average time delay between the ends of sensed atrial events as observed within internal cardiac signals and the ends of corresponding P-waves as observed within a surface electrocardiogram (EKG).

10. The method of claim 1 performed to determine a preferred AV pacing delay value for use in pacing the ventricles subsequent to a paced atrial event (i.e. $A_{PULSE}\text{-}V_{PULSE}$).

11. The method of claim 1 further including the step of delivering pacing therapy using the implantable medical device subject to the preferred AV pacing delay value.

12. The method of claim 1 further including the step of adjusting the preferred AV pacing delay value based on a current patient heart rate.

13. The method of claim 1 wherein the initial AV pacing delay is selected from a range of acceptable initial AV delay values.

14. The method of claim 13 wherein the range of acceptable initial AV pacing delay values includes a minimum acceptable initial AV delay value in the range of 80 to 150 milliseconds (ms).

15. A method for use by an implantable medical device for determining a preferred atrioventricular (AV) delay pacing value for use in delivering cardiac pacing therapy to the heart of a patient in which the device is implanted, the method comprising the steps of:
pacing the heart using an initial AV pacing delay set to a value less than an intrinsic AV conduction delay;
measuring a time delay between the ends of atrial events and the peaks of the subsequent paced ventricular events within an internal electrical cardiac signal sensed by the device between an atrial tip electrode and a case of the implantable device; and
determining the preferred AV pacing delay value based on the initial AV pacing delay, the measured time delay between the end of the atrial event and the peak of the subsequent paced ventricular event, and on a predetermined preferred time delay to be achieved between the end of atrial events and the peaks of subsequent paced ventricular events.

16. A system for use by an implantable medical device for determining a preferred atrioventricular (AV) delay pacing value for use in delivering cardiac pacing therapy to the heart of a patient in which the device is implanted, the system comprising:

a pacing system operative to pace the heart using an initial AV pacing delay set to a value less than an intrinsic AV conduction delay;

a sensing system operative to sense resulting internal electrical cardiac signals sensed between an atrial tip electrode and a case of the implantable device; and an on-board AV delay optimization system operative to measure a time delay between an atrial event and a subsequent paced ventricular event within the internal electrical cardiac signal and to further determine a preferred AV pacing delay value for further pacing based on the initial AV pacing delay, the measured time delay between the atrial event and the subsequent paced ventricular event, and on a predetermined preferred time delay to be achieved between atrial events and subsequent paced ventricular events.

17. A system for use by an implantable medical device for determining a preferred atrioventricular (AV) delay pacing value for use in delivering cardiac pacing therapy to the heart of a patient in which the device is implanted, the system comprising:

means for pacing the heart using an initial AV pacing delay set to a value less than an intrinsic AV conduction delay;

means for measuring a time delay between an atrial event and a subsequent paced ventricular event with an internal electrical cardiac signal sensed between an atrial tip electrode and a case of the implantable device; and means for determining the preferred AV pacing delay value based on the initial AV pacing delay, the measured time delay between the atrial event and the subsequent paced ventricular event, and on a predetermined preferred time delay between atrial events and subsequent paced ventricular events.

* * * * *